US009682169B2

(12) United States Patent
Zeitels et al.

(10) Patent No.: US 9,682,169 B2
(45) Date of Patent: *Jun. 20, 2017

(54) HYDROGELS FOR VOCAL CORD AND SOFT TISSUE AUGMENTATION AND REPAIR

(71) Applicants: The General Hospital Corporation, Boston, MA (US); Massachusetts Institute of Technology, Cambridge, MA (US)

(72) Inventors: Steven M. Zeitels, Newton, MA (US); Robert E. Hillman, Weston, MA (US); Sandeep Sidram Karajanagi, Malden, MA (US); Robert S. Langer, Newton, MA (US)

(73) Assignees: Massachusetts Institute of Technology, Cambridge, MA (US); The General Hospital Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/975,039

(22) Filed: Dec. 18, 2015

(65) Prior Publication Data

US 2016/0175483 A1 Jun. 23, 2016

Related U.S. Application Data

(63) Continuation of application No. 12/553,800, filed on Sep. 3, 2009, now Pat. No. 9,216,188.

(60) Provisional application No. 61/094,237, filed on Sep. 4, 2008.

(51) Int. Cl.
| A61K 31/00 | (2006.01) |
| A61L 27/26 | (2006.01) |
| A61L 27/52 | (2006.01) |
| C08J 3/24 | (2006.01) |
| C08J 3/075 | (2006.01) |
| A61K 31/7052 | (2006.01) |
| A61L 27/38 | (2006.01) |
| A61L 27/50 | (2006.01) |

(52) U.S. Cl.
CPC ............ *A61L 27/26* (2013.01); *A61K 31/00* (2013.01); *A61K 31/7052* (2013.01); *A61L 27/38* (2013.01); *A61L 27/3834* (2013.01); *A61L 27/50* (2013.01); *A61L 27/52* (2013.01); *C08J 3/075* (2013.01); *C08J 3/246* (2013.01); *A61L 2400/06* (2013.01); *A61L 2430/34* (2013.01); *C08J 2305/08* (2013.01); *C08J 2371/02* (2013.01)

(58) Field of Classification Search
CPC .. A61L 27/26; A61L 2430/34; A61L 27/3834; A61L 27/38; A61L 27/50; A61L 27/52; C08L 71/02; A61K 31/00; A61K 31/7052
See application file for complete search history.

(56) References Cited

U.S. PATENT DOCUMENTS

| 2,898,898 | A | 8/1959 | Burch |
| 3,867,329 | A | 2/1975 | Halpern et al. |
| 4,439,584 | A | 3/1984 | Gould et al. |
| 5,549,673 | A | 8/1996 | Beale |
| 5,733,562 | A | 3/1998 | Lee |
| 5,749,968 | A | 5/1998 | Melanson et al. |
| 5,763,399 | A | 6/1998 | Lee |
| 5,844,016 | A | 12/1998 | Sawhney et al. |
| 5,893,830 | A | 4/1999 | Zeitels |
| 5,900,245 | A | 5/1999 | Sawhney et al. |
| 5,919,702 | A | 7/1999 | Purchio et al. |
| 6,051,248 | A | 4/2000 | Sawhney et al. |
| 6,121,341 | A | 9/2000 | Sawhney et al. |
| 6,214,331 | B1 | 4/2001 | Vanderhoff et al. |
| 6,217,894 | B1 | 4/2001 | Sawhney et al. |
| 6,352,710 | B2 | 3/2002 | Sawhney et al. |
| 6,372,494 | B1 | 4/2002 | Naughton et al. |
| 6,387,977 | B1 | 5/2002 | Sawhney et al. |
| 6,432,437 | B1 | 8/2002 | Hubbard |
| 6,455,600 | B1 | 9/2002 | Hahnle et al. |
| 6,531,147 | B2 | 3/2003 | Sawhney et al. |

(Continued)

FOREIGN PATENT DOCUMENTS

| EP | 0 637 450 | 2/1995 |
| EP | 0 815 177 | 1/1998 |

(Continued)

OTHER PUBLICATIONS

Hertegård et al Otolaryngol Head Neck Surg. Mar. 2003;128(3):401-6.*
Hertegård et al Laryngoscope. 2002, 112(12):2211-9.*
Chan et al Laryngoscope, 1091142-1 149,1999.*
Klemuk et al Laryngoscope, 114:1597-1603, 2004.*
Zeitels et al Laryngoscope 111 : 2001, 1862-1865.*
Leach et al (Biomaterials, 2005, 26, 125-135.*
Cruise et al (Cell Transplantation, 1999, 8, 293-306.*
Abelson, M.B., et al., Clinical cure of bacterial conjunctivitis with azithromycin 1%: Vehicle-controlled, double-masked clinical trial. American Journal of Ophthalmology, 2008. 145(6): p. 959-965.

(Continued)

Primary Examiner — Anoop Singh
(74) Attorney, Agent, or Firm — Fish & Richardson P.C.

(57) ABSTRACT

The present invention provides hydrogels and compositions thereof for vocal cord repair or augmentation, as well as other soft tissue repair or augmentation (e.g., bladder neck augmentation, dermal fillers, breast implants, intervertebral disks, muscle-mass). The hydrogels or compositions thereof are injected into the superficial lamina propria or phonatory epithelium to restore the phonatory mucosa of the vocal cords, thereby restoring a patient's voice. In particular, it has been discovered that hydrogels with an elastic shear modulus of approximately 25 Pa are useful in restoring the pliability of the phonatory mucosa. The invention also provides methods of preparing and using the inventive hydrogels.

18 Claims, 4 Drawing Sheets

(56) References Cited

U.S. PATENT DOCUMENTS

| | | |
|---|---|---|
| 6,537,574 B1 | 3/2003 | Hubbard |
| 6,544,503 B1 | 4/2003 | Vanderhoff et al. |
| 6,790,840 B1 | 9/2004 | Lee et al. |
| 6,949,625 B2 | 9/2005 | Tayot |
| 7,060,287 B1 | 6/2006 | Hubbard et al. |
| 7,073,294 B2 | 7/2006 | Yamaska et al. |
| 7,118,746 B1 | 10/2006 | Naughton et al. |
| 7,131,997 B2 | 11/2006 | Bourne et al. |
| 7,238,364 B2 | 7/2007 | Sawhney et al. |
| 7,311,861 B2 | 12/2007 | Lanphere et al. |
| 7,387,032 B2 | 6/2008 | Cliffon et al. |
| 7,412,978 B1 | 8/2008 | Keller |
| 2001/0000728 A1 | 5/2001 | Sawhney et al. |
| 2002/0064512 A1 | 5/2002 | Petersen et al. |
| 2002/0127266 A1 | 9/2002 | Sawhney et al. |
| 2003/0003436 A1 | 1/2003 | Willson et al. |
| 2003/0104032 A1 | 6/2003 | Sawhney et al. |
| 2003/0147835 A1 | 8/2003 | Munro et al. |
| 2003/0175410 A1 | 9/2003 | Campbell et al. |
| 2003/0233150 A1 | 12/2003 | Bourne et al. |
| 2004/0028676 A1 | 2/2004 | Klein et al. |
| 2004/0185021 A1 | 9/2004 | Hubbard |
| 2004/0191900 A1 | 9/2004 | Mizuno et al. |
| 2004/0234574 A9 | 11/2004 | Sawhney et al. |
| 2004/0242770 A1 | 12/2004 | Feldstein et al. |
| 2005/0074877 A1 | 4/2005 | Mao et al. |
| 2005/0142152 A1 | 6/2005 | Leshchiner et al. |
| 2005/0226935 A1 | 10/2005 | Kamath et al. |
| 2005/0238870 A1 | 10/2005 | Buiser et al. |
| 2005/0263916 A1 | 12/2005 | Lanphere et al. |
| 2005/0281866 A1 | 12/2005 | Jarrett et al. |
| 2005/0287180 A1 | 12/2005 | Chen et al. |
| 2006/0084759 A1 | 4/2006 | Calabro et al. |
| 2006/0094944 A1 | 5/2006 | Chuang et al. |
| 2006/0094945 A1 | 5/2006 | Barman et al. |
| 2006/0094946 A1 | 5/2006 | Kellogg et al. |
| 2006/0207343 A1 | 9/2006 | Clifton et al. |
| 2006/0233854 A1 | 10/2006 | Seliktar et al. |
| 2006/0233855 A1 | 10/2006 | Seliktar et al. |
| 2006/0246033 A1 | 11/2006 | Ninan et al. |
| 2007/0015908 A1 | 1/2007 | Fischer et al. |
| 2007/0020225 A1 | 1/2007 | Abramson et al. |
| 2007/0036745 A1 | 2/2007 | Leshchiner et al. |
| 2007/0059375 A1 | 3/2007 | Bourne et al. |
| 2007/0060998 A1 | 3/2007 | Butterwick et al. |
| 2007/0077232 A1 | 4/2007 | Naughton et al. |
| 2007/0141339 A1 | 6/2007 | Song et al. |
| 2007/0141340 A1 | 6/2007 | Song et al. |
| 2007/0142560 A1 | 6/2007 | Song et al. |
| 2007/0179605 A1 | 8/2007 | Myung et al. |
| 2007/0212385 A1 | 9/2007 | David et al. |
| 2007/0225631 A1 | 9/2007 | Bowlin et al. |
| 2007/0270501 A1 | 11/2007 | Fitzgerald et al. |
| 2007/0280986 A1 | 12/2007 | Gil et al. |
| 2007/0283962 A1 | 12/2007 | Doshi et al. |
| 2008/0008647 A1 | 1/2008 | Richard et al. |
| 2008/0009902 A1 | 1/2008 | Hunter et al. |
| 2008/0009942 A1 | 1/2008 | Mizuno et al. |
| 2008/0032920 A1 | 2/2008 | Prestwich et al. |
| 2008/0038306 A1* | 2/2008 | David ............ A61K 8/02 424/422 |
| 2008/0041715 A1 | 2/2008 | Lanphere et al. |
| 2008/0045654 A1 | 2/2008 | Richard et al. |
| 2008/0152698 A1 | 6/2008 | Effing et al. |
| 2009/0042294 A1 | 2/2009 | Calabro et al. |
| 2009/0142309 A1 | 6/2009 | Calabro et al. |
| 2009/0143766 A1 | 6/2009 | Calabro et al. |
| 2009/0252700 A1 | 10/2009 | Zahos et al. |
| 2010/0055184 A1 | 3/2010 | Zeitels |
| 2013/0041467 A1 | 2/2013 | Zeitels et al. |

FOREIGN PATENT DOCUMENTS

| | | |
|---|---|---|
| EP | 0 927 214 | 7/1999 |
| EP | 1 178 812 | 2/2002 |
| EP | 1 534 351 | 6/2005 |
| EP | 1 870 115 | 12/2007 |
| JP | 2006-522851 | 10/2006 |
| WO | 96/29370 | 9/1996 |
| WO | 97/22372 | 6/1997 |
| WO | 98/08550 | 3/1998 |
| WO | 98/12243 | 3/1998 |
| WO | 98/17791 | 4/1998 |
| WO | 99/31167 | 6/1999 |
| WO | 00/44808 | 8/2000 |
| WO | 00/69449 | 11/2000 |
| WO | 01/96422 | 12/2001 |
| WO | 02/063270 | 8/2002 |
| WO | 03/079985 | 10/2003 |
| WO | 03/082359 | 10/2003 |
| WO | 2004/032713 | 4/2004 |
| WO | 2005/018612 | 3/2005 |
| WO | 2005/025493 | 3/2005 |
| WO | 2005/061018 | 7/2005 |
| WO | 2005/097677 | 10/2005 |
| WO | 2005/105906 | 11/2005 |
| WO | 2005/115489 | 12/2005 |
| WO | 2005/118128 | 12/2005 |
| WO | 2006/002050 | 1/2006 |
| WO | 2006/004951 | 1/2006 |
| WO | 2006/022671 | 3/2006 |
| WO | 2006/050031 | 5/2006 |
| WO | 2006/050032 | 5/2006 |
| WO | 2006/050033 | 5/2006 |
| WO | 2006/062253 | 6/2006 |
| WO | 2007/032565 | 3/2007 |
| WO | 2007/004437 | 4/2007 |
| WO | 2007/073553 | 6/2007 |
| WO | 2007/073554 | 6/2007 |
| WO | 2007/089864 | 8/2007 |
| WO | 2007/106457 | 9/2007 |
| WO | 2007/124132 | 11/2007 |
| WO | 2007/126411 | 11/2007 |
| WO | 2008/008859 | 1/2008 |
| WO | 2008/024640 | 2/2008 |
| WO | 2008/041846 | 4/2008 |

OTHER PUBLICATIONS

Adams, M.E. et al., "A risk-benefit of injections of Hyaluronan and its derivatives in the treatment of osteoarthritis of the knee," Drug Safety, 2000; 23:115-130.

Argentiere, S., et al., Synthesis of Poly(acrylic acid) Nanogels and Application in Loading and Release of an Oligothiophene Fluorophore and Its Bovine Serum Albumin Conjugate. Macromolecular Symposia, 2009. 281: p. 69-76.

Bader et al., "A study of diffusion in poly(ethyleneglycol)-gelatin based semi-interpenetrating networks for use in wound healing," Polym. Bull., 2009, 62:381-389.

Barbu, E., et al., Polymeric materials for ophthalmic drug delivery: trends and perspectives. Journal of Materials Chemistry, 2006. 16(34): p. 3439-3443.

Barr et al., Quality of life in children with velopharyngeal insufficiency. Arch Otolaryngol Head Neck Surg. Mar. 2007;133(3):224-9.

Burdick, J.A., et al, Stimulation of neurite outgrowth by neurotrophins delivered from degradable hydrogels. Biomaterials, 2006. 27(3): p. 452-459.

Burugapalli, K., V. Koul, and A. K. Dinda, Effect of composition of interpenetrating polymer network hydrogels based on poly(acrylic acid) and gelatin on tissue response: A quantitative in vivo study. Journal of Biomedical Materials Research Part A, 2004. 68A(2): p. 210-218.

Carpenter, C.P. and C.B. Shaffer, A study of the polyethylene glycols as vehicle for intramuscular and subcutaneous injection. Journal of the American Pharmaceutical Association-Scientific Edition, 1952.41(1): p. 27-29.

Carpenter, C.P., et al, Response of dogs to repeated intravenous injection of polyethylene-glycol-4000 with notes on excretion and

(56) References Cited

OTHER PUBLICATIONS sensitization. Toxicology and Applied Pharmacology, 1971. 18(1): p. 35-40.

Caton et al., Viscoelasticity of hyaluronan and nonhyaluronan based vocal fold injectables: implications for mucosal versus muscle use. Laryngoscope. Mar. 2007;117(3):516-21.

Chan et al., Laryngoscope, 109:1142-1149 (1999).

Chan et al., Viscoelastic Shear Properties of Human Vocal Fold Mucosa: Measurement Methodology and Empirical Results; *J. Acoust. Soc. Am.* 106(4), Pt. 1, Oct. 1999; pp. 2008-2021.

Cho et al., "A novel synthetic route for the preparation of hydrolytically degradable synthetic hydrogels," J Biomed Mater Res., 2009, 90A:1073-1082.

Christensen, L., "Normal and pathologic tissue reactions to soft-tissue gel fillers," Dermatologic Surgery, 2007; 33:S168-S175.

Cobell et al., Fine needle aspiration of the vocal fold lamina propria in an animal model. Ann Otol Rhinol Laryngol. Oct. 2006;115(10):764-8.

Cobell et al., Fine needle aspiration: a novel application in laryngology. J Voice. Sep. 2007;21(5):617-22.

Connor et al., Attitudes of children with dysphonia. J Voice. Mar. 2008;22(2):197-209.

Cruise, G.M., et al., In vitro and in vivo performance of porcine islets encapsulated in interfacially photopolymerized poly(ethylene glycol) diacrylate membranes. Cell Transplantation, 1999.8(3): p. 293-306.

Delong et al., Covalently immobilized gradients of bFGF on hydrogel scaffolds for directed cell migration. Biomaterials. Jun. 2005;26(16):3227-34.

Duflo et al., Differential gene expression profiling of vocal fold polyps and Reinke's edema by complementary DNA microarray. Ann Otol Rhinol Laryngol. Sep. 2006;115(9):703-14.

Duflo et al., Effect of a synthetic extracellular matrix on vocal fold lamina propria gene expression in early wound healing. Tissue Eng. Nov. 2006;12(11):3201-7.

Duflo et al., Vocal fold tissue repair in vivo using a synthetic extracellular matrix. Tissue Eng. Aug. 2006;12(8):2171-80.

Elbert, D.l. and J.A. Hubbell, Conjugate addition reactions combined with free-radical cross-linking for the design of materials for tissue engineering. Biomacromolecules, 2001. 2(2): p. 430-41.

European Office Action in Application No. 09 81 836.7, dated Apr. 18, 2013, 6 pages.

Ferguson et al., Time and dose effects of mitomycin C on extracellular matrix fibroblasts and proteins. Laryngoscope. Jan. 2005;115(1):110-5.

Fisher et al., Photoinitiated polymerization of biomaterials. Annu Rev Mater Res. 2001;31:171-181.

Gable, R.S., Comparison of acute lethal toxicity of commonly abused psychoactive substances. Addiction, 2004. 99(6): p. 686-696.

Gobin et al., Val-ala-pro-gly, an elastin-derived non-integrin ligand: smooth muscle cell adhesion and specificity. J Biomed Mater Res A. Oct. 1, 2003;67(1):255-9.

Goodyer et al., In Vivo Measurement of the Shear Modulus of the Human Vocal Fold: Interim Results From Eight Patients; *Eur Arch Otorhinolaryngol*, 2006; DOI 10.1007/s00405-006-0239-z.

Goodyer et al., The Shear Modulus of the Human Vocal Fold, Preliminary Results from 20 Larynxes, *Eur Arch Otorhinolaryngol*, 2007, 264:45-50.

Hahn, M.S., et al., Glycosaminoglycan composition of the vocal-fold lamina propria in relation to function. Annals of Otology Rhinology and Laryngology, 2008. 117(5): p. 371-381.

Hansen et al., Current understanding and review of the literature: vocal fold scarring. J Voice. Mar. 2006;20(1):110-20.

Hansen et al., In vivo engineering of the vocal fold extracellular matrix with injectable hyaluronic acid hydrogels: early effects on tissue repair and biomechanics in a rabbit model. Ann Otol Rhinol Laryngol. Sep. 2005;114(9):662-70.

Hertegard et al., Acta Otolaryngol, 124:1208-1214 (2004).

Hertegard et al., Laryngoscope, 112(12):2211-2219 (2002).

Hertegard et al., Otolaryngol Head Neck Surg., 128(3):401-406 (Mar. 2003).

Herten, M., et al., Biodegradation of different synthetic hydrogels made of polyethylene glycol hydrogel/RGD-peptide modifications: an immunohistochemical study in rats. Clin. Oral Implants Res, 2009. 20(2): p. 116-25.

Hillman, R.E., The Contempory Voice Laboratory: Its Role in the Diagnosis of Laryngeal Disorders, in Otolaryngology-Head and Neck Surgery Recertification Study Guide, J. Gluckman, Editor. 1999.

Hillman, R.E., W.M. Montgomery, and S.M. Zeitels, Current Diagnostics and Office Practice: Use of objective measures of vocal function in the multidisciplinary management of voice disorders. Current Opinion in Otolaryngology & Head and Neck Surgery 1997. 5(3): p. 172-175.

Hirano et al., Structure of the vocal fold in normal and diseased states: anatomical and physical studies. Proceedings of the Conference on the Assessment of Vocal Pathology. The American Speech-Language-Hearing Association. 1981;11:11-27.

Hirano, S., et al, Growth factor therapy for vocal-fold scarring in a canine model. Annals of Otology Rhinology and Laryngology, 2004. 113(10): p. 777-785.

Hogikyan, N.D. and G. Sethuraman, Validation of an instrument to measure voice-related quality of life (V-RQOL). Journal of Voice, 1999. 13: p. 557-569.

Ifkovits, J.L and J.A. Burdick, Review: Photopolymerizable and degradable biomaterials for tissue engineering applications. Tissue Engineering, 2007.13(10): p. 2369-2385.

International Preliminary Report on Patentability; PCT/US2009/004974; Simin Baharlou; Mar. 8, 2011.

International Preliminary Report on Patentability; PCT/US2011/027230; Sep. 4, 2012.

International Search Report and Written Opinion; PCT/US2009/004974; N.Y. Jang; Apr. 2010.

Jackson, C., Position of the Patient for Peroral Endoscopy, in Peroral Endoscopy and Laryngeal Surgery. 1915, Laryngoscope Co.: St. Louis. p. 77-88.

Jia et al., Hyaluronic Acid-Based Microgels and Microgel Networks for Vocal Fold Regeneration; *Biomacromolecules* 2006, 7, pp. 3336-3344.

Jia et al., Synthesis and Characterization of In Situ Cross-Linkable Hyaluronic Acid-Based Hydrogels with Potential Application for Vocal Fold Regeneration; *Macromolecules* 2004, 37, pp. 3239-3248.

Jones, D.S., et al., Physicochemical characterization of bioactive polyacrylic acid organogels as potential antimicrobial implants for the buccal cavity. Biomacromolecules, 2008.9(2): p. 624-633.

Kass, E.5., Hillman, R.E., Zeitels, S.M., The Submucosal Infusion Technique in Phonomicrosurgery. Annals of Otology, Rhinology, & Laryngology, 1996. 105: p. 341-347.

Kempster, G., et al., Consensus Auditory-Perceptual Evaluation of Voice: Development of a Standardized Clinical Protocol American Journal of Speech-Language Pathology, 2009. 18(2): p. 124-132.

Kim et al., Synthesis and evaluation of novel biodegradable hydrogels based on poly(ethylene glycol) and sebacic acid as tissue engineering scaffolds. Biomacromolecules. Jan. 2008;9(1):149-57.

Kizilel et al., Sequential formation of covalently bonded hydrogel multilayers through surface initiated photopolymerization. Biomaterials. Mar. 2006;27(8):1209-15.

Kizilel, S., V.H. Perez-Luna, and F. Teymour, Photopolymerization of poly(ethylene glycol) diacrylate on eosin-functionalized surfaces. Langmuir, 2004. 20(20): p. 8652-8658.

Klemuk et al., Laryngoscope, 114:1597-1603 (2004).

Ko et al., Photo-crosslinked porous PEG hydrogel membrane via electrospinning. J Photopolym Sci Technol. 2006;19(3):413-18.

Kriesel et al., Treatment of vocal fold scarring: rheological and histological measures of homologous collagen matrix. Ann Otol Rhinol Laryngol. Oct. 2002;111(10):884-9.

Kutty, J.K. et al.; Mechanomimetic Hydrogels for Vocal Fold Lamina Propria Regeneration; J. Biomat.; Sci Polym. Ed. 2009, 20(5-6) p. 737-56.

(56) References Cited

OTHER PUBLICATIONS

Kutty, J.K.; Vibration stimulates vocal mucosa-like matrix expression by hydrogel-encapsulated ; J tissue Eng Regen Med.; 2010;4(1) 62-72.
Kutty, K.J., et al., The effect of hyaluronic acid incorporation on fibroblast spreading and proliferation within PEG-diacrylate based semi-interpenetrating networks. Biomaterials, 2007. 28(33): p. 4928-4938.
Leach et al., Biomaterials, 26:125-135 (2005).
Mehta, D.D., et al, Voice production mechanisms following phonosurgical treatment of early glottic cancer. Annals of Otology, Rhinology & Laryngology, 2010. 119: p. 1-9.
Moon et al., Promotion of endothelial tubulogenesis with Ephrin A1 and EphB4 conjugated to synthetic hydrogels. FASEB J. Mar. 6, 2006;20(4):A12.
Munoz-Pinto et al., "Probing Vocal Fold Fibroblast Response to Hyaluronan in #D Contexts," Biotechnol. Bioeng., Nov. 1, 2009, 104(4):821-831.
Myung, D. et al.; Biomimetic strain hardening in interpenetrating polymer network hydrogels; ScienceDirect; vol. 48, Issue 18; Aug. 24, 2007, p. 5376-5387.
Nuttelman et al., The effect of ethylene glycol methacrylate phosphate in PEG hydrogels on mineralization and viability of encapsulated hMSCs. Biomaterials. Mar. 2006;27(8):1377-86.
Orlandi et al., Microarray analysis of allergic fungal sinusitis and eosinophilic mucin rhinosinusitis. Otolaryngol Head Neck Surg. May 2007;136(5):707-13.
Park, V.D., N. Tirelli, and J.A. Hubbell, Photopolymerized hyaluronic acid-based hydrogels and interpenetrating networks. Biomaterials, 2003. 24(6): p. 893-900.
Prestwich et al., Injectable synthetic extracellular matrices for tissue engineering and repair. Adv Exp Med Biol. 2006;585:125-33.
Ramanan et al., Development of a temperature-sensitive composite hydrogel for drug delivery applications. Biotechnol Prog. Jan.-Feb. 2006;22(1):118-25.
Restriction Requirement in U.S. Appl. No. 13/579,347, dated Oct. 11, 2013, 7 pages.
Rousseau et al., Experimentally induced phonation increases matrix metalloproteinase-1 gene expression in normal rabbit vocal fold. Otolaryngol Head Neck Surg. Jan. 2008;138(1):62-8.
Rousseau, B., et al, Characterization of vocal-fold scarring in a canine model. Laryngoscope, 2003. 113(4): p. 620-627.
Roy S., et al., Polymers in Mucoadhesive Drug-Delivery Systems: A Brief Note. Designed Monomers and Polymers, 2009. 12(6): p. 483-495.
Roy, N., et al., Voice disorders in the general population: prevalence, risk factors, and occupational impact. Laryngoscope, 2005.115(11): p. 1988-95.
Scalco, A.N., Shipman, W.F., Tabb, H.G., Microscopic Suspension Laryngoscopy. Annals of Otology, Rhinology, & Laryngology, 1960.69: p. 1134-1138.
Scherzer, T. and U. Decker, Kinetic investigations on the UV-induced photopolymerization of a diacrylate by time-resolved FTIR spectroscopy: the influence of photoinitiator concentration, light intensity and temperature. Radiation Physics and Chemistry, 1999. 55(5-6): p. 615-619.
Shaffer, C.B. and F.H. Critchfield, The Absorption and Excretion of the Solid Polyethylene Glycols (Carbowax Compounds). Journal of the American Pharmaceutical Association-Scientific Edition, 1947. 36(5): p. 152-157.
Shaffer, C.B., F.H. Critchfield, and C.P. Carpenter, Renal Excretion and Volume Distribution of Some Polyethylene Glycols in the Dog. American Journal of Physiology, 1948. 152(1): p. 93-99.
Si, E.C., et al., Ocular Pharmacokinetics of AzaSite Xtra-2% Azithromycin Formulated in a DuraSite Delivery System. Current Eye Research, 2009. 34(6): p. 485-491.
Smyth, H.F., C.P. Carpenter, and C.B. Shaffer, The Toxicity of High Molecular Weight Polyethylene Glycols-Chronic Oral and Parenteral Administration. Journal of the American Pharmaceutical Association-Scientific Edition, 1947. 36(5): p. 157-160.
Supplementary European Search Report issued in EP09811836 on Feb. 21, 2013.
Supplementary European Search Report; EP 09 81 1836; Feb. 21, 2013; D. Werner; pp. 1-3.
Taite et al., Bioactive hydrogel substrates: probing leukocyte receptor-ligand interactions in parallel plate flow chamber studies. Ann Biomed Eng. Nov. 2006;34(11):1705-11.
Thibeault et al., Comparison of telomere length of vocal folds with different tissues: a physiological measurement of vocal senescence. J Voice. Jun. 2006;20(2):165-70.
Thibeault et al., Gene expression changes of inflammatory mediators in posterior laryngitis due to laryngopharyngeal reflux and evolution with PPI treatment: a preliminary study. Laryngoscope. Nov. 2007;117(11):2050-6.
Thibeault et al., Inflammatory cytokine responses to synthetic extracellular matrix injection to the vocal fold lamina propria. Ann Otol Rhinol Laryngol. Mar. 2008;117(3):221-6.
Thibeault et al., Informed consent in otolaryngology research. Otolaryngol Head Neck Surg. Nov. 2005;133(5):651-3.
Thibeault, Advances in our understanding of the Reinke space. Curr Opin Otolaryngol Head Neck Surg. Jun. 2005;13(3):148-51.
U.S. Office Action in U.S. Appl. No. 13/579,347, dated Jan. 13, 2015, 12 pages.
U.S. Office Action in U.S. Appl. No. 13/579,347, dated May 21, 2014, 12 pages.
West, J.L. et al., "Separation of the arterial wall from blood contact using hydrogel barriers reduces intimal thickening after balloon injury in the rat: the roles of medial and luminal factors in arterial healing," Proc. Natl. Acad. Sci., USA, 1996; 93:13188-93.
Williams, C.G., et al., Variable cytocompatibility of six cell lines with photoinitiators used for polymerizing hydrogels and cell encapsulation. Biomaterials, 2005. 26(11): p. 1211-1218.
Wlotzka et al., In vivo properties of an anti-GnRH Spiegelmer: an example of an oligonucleotide-based therapeutic substance class. Proc Natl Acad Sci U S A. Jun. 25, 2002;99(13):8898-902.
Working, P.K., et l., Safety of poly(ethylene glycol) and poly(ethylene glycol) derivatives, in Poly(Ethylene Glycol), Chemistry and Biological Applications, J.M. Harris and S. Zalipskv, Editors. 1997. p. 45-57.
Ylitalo et al., Relationship between time of exposure of laryngopharyngeal reflux and gene expression in laryngeal fibroblasts. Ann Otol Rhinol Laryngol. Oct. 2006;115(10):775-83.
Zeitels et al., Foresight in laryngology and laryngeal surgery: a 2020 vision. Ann Otol Rhinol Laryngol. 2007;116(Supplement 198):1-16.
Zeitels et al., Laryngology and phonosurgery. N Engl J Med. Aug. 28, 2003;349(9):882-92.
Zeitels et al., Phonomicrosurgery in singers and performing artists: treatment outcomes, management theories, and future directions. Ann Otol Rhinol Laryngol. 2002;111(Supplement 190):21-40.
Zeitels et al., Phonosurgical reconstruction of early glottic cancer. Laryngoscope. Oct. 2001;111(10):1862-5.
Zeitels et al., Sulcus, scar, synechia, and web. In Atlas of Phonomicrosurgery and Other Endolaryngeal Procedures for Benign and Malignant Disease. 2001; Singular, San Diego:133-151.
Zeitels et al., Voice and treatment outcome from phonosurgical management of early glottic cancer. Ann Otol Rhinol Laryngol. 2002;111(Supplement 190):1-20.
Zeitels, S.M., A Universal Modular Glottiscope System: The Evolution of a Century of Design and Technique for Direct Laryngoscopy. Annals of Otology, Rhinology and Laryngology, 1999. 108{Supplement 179): p. 1-24.
Zeitels, S.M., Burns, J. A., Dailey, S. H., Suspension laryngoscopy revisited Annals of Otology, Rhinology, & Laryngology, 2004. 113(1): p. 16-22.
Zeitels, S.M., Premalignant epithelium and microinvasive cancer of the vocal-fold: The evolution of phonomicrosurgical management. Laryngoscope, 1995. 105{Supplement 67): p. 1-51.
Zeitels, S.M., Vaughan, C.W., "External Counter-Pressure" and "Internal Distension" for Optimal Laryngoscopic Exposure of the Anterior Glottal Commissure. Annals of Otology, Rhinology & Laryngology, 1994. 103: p. 669-675.

(56) References Cited

OTHER PUBLICATIONS

Zeitels, S.M., Vaughan, C.W., A submucosal vocal-fold infusion needle. Otolaryngology: Head and Neck Surgery, 1991. 105: p. 478-479.
Restriction Requirement issued in U.S. Appl. No. 12/553,800 on Dec. 23, 2011 (8 pages).
Non-Final Office Action issued in U.S. Appl. No. 12/553,800 on Mar. 30, 2012 (19 pages).
Final Office Action issued in U.S. Appl. No. 12/553,800 on Jan. 7, 2013 (19 pages).
Non-Final Office Action issued in U.S. Appl. No. 12/553,800 on Oct. 27, 2014 (20 pages).

\* cited by examiner

HYDROGELS FOR VOCAL CORD AND SOFT TISSUE AUGMENTATION AND REPAIR

RELATED APPLICATIONS

The present application claims priority under 35 U.S.C. §119(e) to U.S. provisional patent application, U.S. Ser. No. 61/094,237, filed Sep. 4, 2008, which is incorporated herein by reference.

BACKGROUND OF THE INVENTION

The vocal folds are the primary vibratory tissues essential for voice production. In humans, there are two vocal folds, each consisting of a stratified squamous epithelium, which encapsulates the lamina propria (LP) and the vocalis muscle (Hirano, *Phonosurgery: Basic and Clinical Investigations*. Otologia (Fukuoka), 1975. 21: p. 239-442; Hirano, *Structure of the vocal fold in normal and diseased states: anatomical and physical studies*. Proceedings of the Conference on the Assessment of Vocal Pathology; The American Speech-Language-Hearing Association, 1981. 11: p. 11-27; each of which is incorporated herein by reference). The lamina propria is a soft tissue that can be roughly divided into three layers: superficial, intermediate, and deep. The vocal ligament is comprised of the intermediate and deep layers of the lamina propria, and the vocal muscle is situated deep to the vocal ligament. See FIGS. 1a-1b. Vocal cord mucosa (i.e., the superficial lamina propria and the overlying epithelium) has long been recognized as the key vibratory layer critical for normal phonation (Bishop, J., *Experimental Researches into the Physiology of the Human Voice*. The London & Edinburgh Philosophical Magazine & Journal of Science, 1836; incorporated herein by reference). The superficial lamina propria (SLP) is a relatively acellular and pliable soft tissue and is the key constituent of the phonatory mucosa responsible for vibration. It must be identified, assessed, and preserved in most voice surgical procedures (Zeitels, S. M., Hillman, R. E., Franco, R. A., Bunting, G., *Voice and Treatment Outcome from Phonosurgical Management of Early Glottic Cancer*. Annals of Otology, Rhinology and Laryngology, 2002. 111(Supplement 190): p. 1-20; Zeitels, S. M., Hillman, R. E., Desloge, R. B., Mauri, M., Doyle, P. B., *Phonomicrosurgery in Singers & Performing Artists: Treatment Outcomes, Management Theories, & Future Directions*. Annals of Otology, Rhinology, & Laryngology, 2002. 111(Supplement 190): p. 21-40; Zeitels, S. M., Healy, G. B., *Laryngology and Phonosurgery*. New England Journal of Medicine, 2003. 349(9): p. 882-92; each of which is incorporated herein by reference). Diminished pliability of vocal cord mucosa typically results in permanent hoarseness (Zeitels, S. M., Hillman, R. E., Franco, R. A., Bunting, G., *Voice and Treatment Outcome from Phonosurgical Management of Early Glottic Cancer*. Annals of Otology, Rhinology and Laryngology, 2002. 111(Supplement 190): p. 1-20; Zeitels, S. M., Hillman, R. E., Desloge, R. B., Mauri, M., Doyle, P. B., *Phonomicrosurgery in Singers & Performing Artists: Treatment Outcomes, Management Theories, & Future Directions*. Annals of Otology, Rhinology, & Laryngology, 2002. 111(Supplement 190): p. 21-40; Zeitels, S. M., Healy, G. B., *Laryngology and Phonosurgery*. New England Journal of Medicine, 2003. 349(9): p. 882-92; each of which is incorporated herein by reference). This diminished pliability can result from benign tumors, malignant tumors, diseases, and intubation (e.g., for anesthesia or prolonged intensive care unit respiratory support). Even self-induced insult to the vocal folds in the form of excessive speaking (phonotrauma) over an extended period of time or environmental insults such as smoke, alcohol, or stomach acid from reflux disease can result in stiffening and scarring of the superficial lamina propria. One of the most common defects is the deposition of subepithelial type I collagen in the vocal cord phonatory mucosa resulting in scarring of the SLP.

There have been attempts to restore the SLP using autograft fat tissue, but such attempts have had limited success (Zeitels, S. M., *Sulcus, Scar, Synechia, and Web, in Atlas of Phonomicrosurgery and Other Endolaryngeal Procedures for Benign and Malignant Disease*. 2001, Singular: San Diego. p. 133-151; incorporated herein by reference). Currently, there has been no clinically feasible and reproducible method that has been demonstrated to restore SLP pliability, thereby repairing phonatory mucosal stiffness and eliminating or reducing the associated hoarseness. To date there is simply no synthetic material or autograft that will restore lost pliability to phonatory mucosa to resolve the disordered vocal cord vibration and the associated permanent hoarseness (Zeitels, S. M., Blitzer, A., Hillman, R. E., Anderson, R. R., *Foresight in Laryngology and Laryngeal Surgery: A 2020 Vision*. Ann Otol Rhinol Laryngol, 2007. 116 (Supplement 198): p. 1-16; incorporated herein by reference). All current strategies just change the shape and position of the dysfunctional vocal fold to achieve better valvular closure (Zeitels, S. M., Jarboe, J., Franco, R. A., *Phonosurgical Reconstruction of Early Glottic Cancer*. Laryngoscope, 2001. 111: p. 1862-1865; Kriesel, K. J., Thibeault, S. L., Chan, R. W., Suzuki, T., VanGroll, P. J., Bless, D. M., Ford, C. N., *Treatment of vocal fold scarring: Rheological and histological measures of homologous collagen matrix*. Annals of Otology, Rhinology, and Laryngology, 2002. 111: p. 884-889; each of which is incorporated herein by reference). These techniques enhance voice formation by diminishing aerodynamic incompetency, a surgical maneuver that was done for the first time almost a century ago (Brunings, W., *Eine neue Behandlungsmethode der Rekurrenslahmungen*. Verhandl Deutsch Vereins Deutscher Laryngologen, 1911. 18:93-151; which is incorporated herein by reference). These strategies only achieve severely limited results and do not address the anatomic, physiologic, and/or biomechanical deficit.

SUMMARY OF THE INVENTION

The present invention provides a system for repairing the pliability of the phonatory mucosa of a subject using hydrogels. The system involves inserting or injecting a hydrogel or other material into the subepithelial phonatory mucosal region where the superficial lamina propria is missing (e.g., after successful treatment of vocal cord cancer) or has diminished functional vibratory capacity (e.g., chronic hoarseness from voice overuse and/or smoking). This is done to restore phonatory mucosal pliability and normal vocal cord vibration, thereby reducing stiffness and the associated hoarseness. It has been discovered that hydrogels with an elastic shear modulus of approximately 25 Pa are particularly useful in the inventive system for vocal cord repair. The hydrogels useful in the present invention are typically semi-interpenetrating networks formed when one polymer is cross-linked with itself in the presence of a non-crosslinkable polymer. The invention provides novel hydrogel compositions useful in the inventive system for vocal cord repair as well as methods and apparatuses for delivering the hydrogel to a space created just under or within the superficial lamina propria. The injected hydrogel acts to augment the phonatory mucosa allowing this tissue to vibrate and produce sound. Other materials such as, but not limited to, viscosupplements (e.g., HYALGAN® (sodium hyaluronate), SYNVISC® (Hylan G-F 20), ORTHOVISC® (high molecular weight hyaluronan)) and dermal fillers (e.g., RESTYLANE® (hyaluronic acid), PERLANE® (hyaluronic acid), HYLAFORM® (stabilized hyaluronic acid), RADIESSE® (calcium hydroxylapatite microspheres in a water-based gel)) may also be used for vocal cord repair. As will be appreciated by one of skill in the art, the hydrogels described herein are also useful in repairing and/or augmenting other soft tissues. For example, the hydrogels may be used as deep vocal cord implants (paraglottic muscles) for medialization (e.g., paralytic dysphonia), dermal fillers, breast implants, bladder neck implants for incontinence, intervertebral disks, muscle mass, facial contouring, and joint fluid. It may also be used for packing wounds or incisions including orifices such as the nose and ear.

In one aspect, the invention provides novel hydrogels for use in the present system for vocal cord repair, or other soft tissue repair or augmentation. These novel hydrogels may provide immediate reconstitution of the vocal cord, which may be long-lasting or temporary, and the hydrogel may provide a substrate or scaffold to introduce cells (e.g., pluripotent cells such as stem cells) or other biologically active agents (e.g., drugs). For example, a dissolving hydrogel may be reinserted/reinjected in the operating room or the clinic every 2-3 months, or every 6 months as needed by the subject, which is similar to patients who are administered periodic injections of Botox (botulinum toxin) to treat spasmodic dysphonia. Hydrogels useful in the present invention are typically semi-interpenetrating networks of polymers although interpenetrating networks of polymers and one-component hydrogels may also find use in the present invention. The hydrogels have an elastic shear modulus ranging from approximately 15 Pa to approximately 35 Pa. In certain embodiments, the elastic shear modulus ranges from approximately 20 Pa to approximately 30 Pa. In certain embodiments, the elastic shear modulus of the hydrogel is approximately 25 Pa. In certain embodiments, the hydrogel comprises acrylated polyethylene glycol and another water-soluble non-crosslinkable polymer (e.g., polyethylene glycol, proteins, hyaluronic acid, collagen, polylysine, dextran, alginates, gelatin, elastin, cellulose, etc.). In certain embodiments, the hydrogel comprises a cross-linkable protein or peptide (e.g., cross-linkable derivatives of elastin-like peptides, collagen-mimetic peptides, collagen-related peptides, polylysine) or a cross-linkable polysaccharide (e.g., cross-linkable derivatives of hyaluronic acid, methyl cellulose, dextran, alginate, etc.). In certain embodiments, the hydrogel comprises a cross-linkable elastomeric polymer (e.g., cross-linkable derivative of poly glycerol sebacate). The cross-linkable peptide, protein, or polysaccharide may include an acrylate moiety for cross-linking. Various polymers, molecular weights, extent of cross-linking, concentrations, cross-linkable moieties, and ratio of crosslinkable versus non-crosslinkable polymers may be utilized in the present invention. In certain embodiments, the crosslinkable polymer component of the hydrogel is cross-linked using photo-crosslinking (e.g., using UV light). In certain embodiments, the crosslinkable polymer component of the hydrogel is cross-linked using a free-radical reaction. Such a free radical reaction may be initiated using light, heat, or a biological or chemical catalyst. In certain embodiments, the free radical reaction is initiated using heat. In certain embodiments, the free radical reaction is initiated using light (e.g., UV light). The hydrogel is typically biocompatible and is not readily biodegradable so that it has an extended half-life in vivo at the site of injection. Biologically active agents, such as cells, polynucleotides, proteins, pharmaceutical agents, etc., or microparticles, nanoparticles, or other drug delivery devices containing any of these biologically active agents may be added to the hydrogel.

In yet another aspect, the invention provides kits useful in treating a patient in need of vocal cord repair. The kit may include all or a subset of all the components necessary for treating a patient. The kits may include, for example, the hydrogel, components of the hydrogel, cross-linking reagent, UV lamp, syringe, needle, anesthetics, antibiotics, etc. In certain embodiments, the components of the kit are sterilely packaged for convenient use by the surgeon or other health care professional. The kit may also include instructions for administering the hydrogel. The kit may provide the necessary components for a single use. The kit may also include packaging and information as required by a governmental regulatory agency that regulates pharmaceuticals and/or medical devices.

BRIEF DESCRIPTION OF THE DRAWING

FIG. 1A is a cephalad view of the laryngeal introitus and vocal folds from the oropharynx. FIG. 1B shows a coronal section of the vocal folds showing their layered microstructure during phonation at low pitch and high pitch. The top of each figure is cephalad anatomically.

DEFINITIONS

Figure 1A:
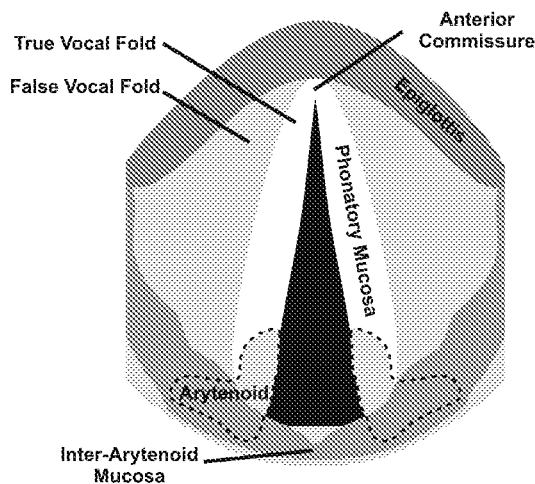
FIG. 1A-B.
Figure 1B:
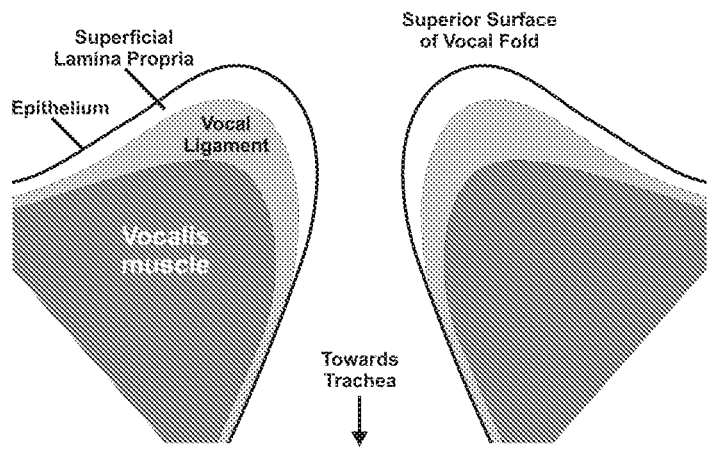
Figure 2:
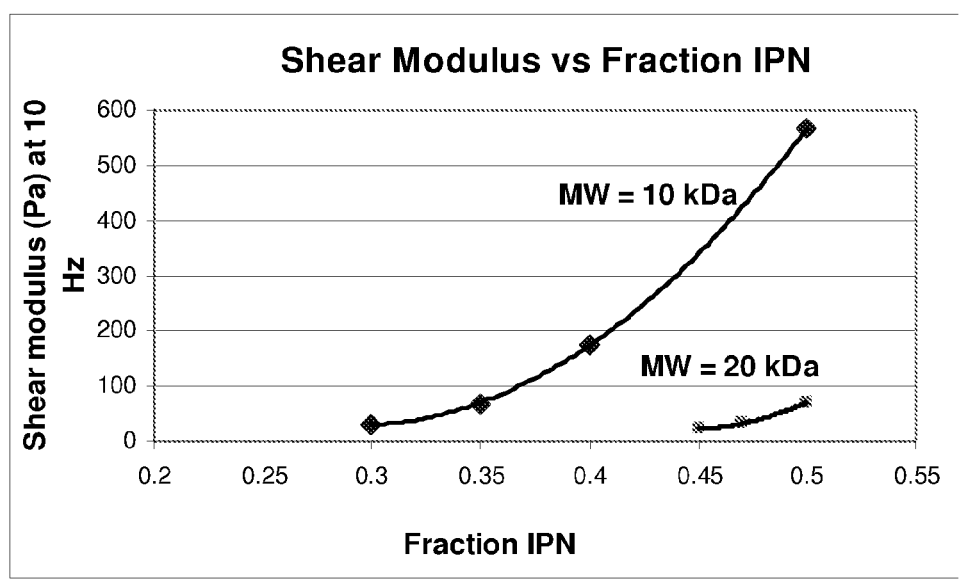
FIG. 2. Dependence of elastic shear modulus of the hydrogels on the fraction of polyethylene glycol-diacrylate (PEG-DA) present in the interpenetrating network. The second component of the interpenetrating network is polyethylene glycol (PEG). The elastic shear modulus strongly depends not only on the fraction of PEG-DA but also on the molecular weights of the components.

"Anti-inflammatory agent," as used herein, refers to any substance that inhibits one or more signs or symptoms of inflammation.

"Anti-fibrotic agent," as used herein, refers to any substance that inhibits fibrosis. An exemplary anti-fibrotic agent is rapamycin.

An "aqueous medium" as used herein means a liquid medium containing water and, optionally, one or more water-miscible solvents (e.g., dimethylformamide (DMF), dimethylsulfoxide (DMSO), and hydrocarbyl alcohols, diols, or glycerols). An aqueous medium may contain at least 50%, 60%, 70%, 80%, 90% or more water by volume. It will be appreciated that an aqueous medium may contain a variety of substances dissolved, dispersed, or suspended therein.

The term "approximately" in reference to a number generally includes numbers that fall within a range of 5% in either direction of the number (greater than or less than the number) unless otherwise stated or otherwise evident from the context (except where such number would exceed 100% of a possible value).

"Biocompatible" refers to a material that is substantially nontoxic to a recipient's cells in the quantities and at the location used, and also does not elicit or cause a significant deleterious or untoward effect on the recipient's body at the location used, e.g., an unacceptable immunological or inflammatory reaction, unacceptable scar tissue formation, etc.

"Biocomparable" refers to a material that does not result in deterioration of normal function of residual or partially functioning tissue in the region in which the material is placed.

"Biodegradable" means that a material is capable of being broken down physically and/or chemically within cells or within the body of a subject, e.g., by hydrolysis under physiological conditions and/or by natural biological processes such as the action of enzymes present within cells or within the body, and/or by processes such as dissolution, dispersion, etc., to form smaller chemical species which can typically be metabolized and, optionally, used by the body, and/or excreted or otherwise disposed of. For purposes of the present invention, a polymer or hydrogel whose molecular weight decreases over time in vivo due to a reduction in the number of monomers is considered biodegradable. In certain embodiments, the hydrogel useful in vocal cord repair is not substantially biodegradable.

A "biologically active agent" is any compound or agent, or its pharmaceutically acceptable salt, which possesses a desired biological activity, for example therapeutic, diagnostic, and/or prophylactic properties in vivo. It is to be understood that the agent may need to be released from the hydrogel in order for it to exert a biological activity. Biologically active agents include, but are not limited to, therapeutic agents as described herein. Biologically active agents may be, without limitation, small molecules, peptides or polypeptides, immunoglobulins, e.g., antibodies, nucleic acids, cells, tissue constructs, etc. Without limitation, hormones, growth factors, drugs, cytokines, chemokines, clotting factors and endogenous clotting inhibitors, etc., are biologically active agents.

The term "crosslinked" as used herein describes a polymer with at least one covalent bond that is not found in the repeating units of the polymer or found between repeating units of the polymer. The crosslinking bonds are typically between individual strands or molecules of the polymer; however, intramolecular crosslinking to form macrocyclic structures may also occur. The crosslinks are formed between any two functional groups of the polymer (e.g., at the ends, on the side chains, etc.). In certain embodiments, the crosslinks are formed between terminal acrylate units of the polymers. Also, any type of covalent bond may form the crosslink (e.g., carbon-carbon, carbon-oxygen, carbon-nitrogen, oxygen-nitrogen, sulfur-sulfur, oxygen-phosphorus, nitrogen-nitrogen, oxygen-oxygen, etc.). The resulting crosslinked material may be branched, linear, dendritic, etc. In certain embodiments, the crosslinks form a 3-D network of crosslinks. The crosslinks may be formed by any chemical reaction that results in the covalent bonds. Typically, the crosslinks are created by free radical initiated reactions, for example, with a photoinitiator or thermal initiator.

The term "endoscope" or "laryngoscope" means an instrument used to direct the placement of the hydrogel in the correct layer of the vocal fold. There are generally three types of laryngoscopes. A rigid telescope with angulated optics similar to a laryngeal mirror may be placed through the mouth to the oropharynx to view the vocal cords. A flexible laryngoscope is passed through the nose into the pharynx to view the vocal cords. A direct laryngoscope is comprised of a rigid spatula or tubular speculum, which is passed through the patient's mouth, typically used during an unconscious state, for visualizing and instrumenting the vocal folds during endoscopic laryngeal surgery or for intubating a patient for general anesthesia or airway support.

A "hydrogel" is a three-dimensional network comprising hydrophilic polymers that contains a large amount of water. A hydrogel may, for example contain 30%, 40%. 50%, 60%, 70%, 80%, 90%, 95%, or an even greater amount of water on a w/w basis. A "hydrogel precursor" is a polymer that is at least partly soluble in an aqueous medium and is capable of becoming crosslinked to form a hydrogel.

"Interpenetrating network" refers to any material with a network of polymers where two polymers are cross-linked in the presence of each other. Both polymers are cross-linkable, and each forms its own network by cross-linking with itself but not with the other polymer. Typically, the two polymers are synthesized and/or cross-linked in the presence of each other, the polymers have similar kinetics, and the two polymers are not dramatically phase separated.

The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least two nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, 2'-methoxyribose, 2'-aminoribose, ribose, 2'-deoxyribose, arabinose, and hexose), or modified phosphate groups (e.g., phosphorothioates and 5'-N phosphoramidite linkages). Enantiomers of natural or modified nucleosides may also be used. Nucleic acids also include nucleic acid-based therapeutic agents, for example, nucleic acid ligands, siRNA, short hairpin RNA, antisense oligonucleotides, ribozymes, aptamers, and SPIEGELMERS™, oligonucleotide ligands described in Wlotzka, et al., *Proc. Natl. Acad. Sci. USA,* 2002, 99(13): 8898, the entire contents of which are incorporated herein by reference.

A "polypeptide", "peptide", or "protein" comprises a string of at least three amino acids linked together by peptide bonds. The terms "polypeptide", "peptide", and "protein", may be used interchangeably. Peptide may refer to an individual peptide or a collection of peptides. Inventive peptides preferably contain only natural amino acids, although non natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

The terms "polysaccharide" and "carbohydrate" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose. (e.g., 2'-fluororibose, deoxyribose, and hexose). Carbohydrates useful in the present invention may be linear or branched. Carbohydrates may exist in many different forms, for example, conformers, cyclic forms, acyclic forms, stereoisomers, tautomers, anomers, and isomers.

"Semi-interpenetrating network" refers to a network of polymers where one polymer is cross-linked with itself in the presence of a non-crosslinkable polymer.

"Small molecule" refers to organic compounds, whether naturally-occurring or artificially created (e.g., via chemical synthesis) that have relatively low molecular weight and that are not proteins, polypeptides, or nucleic acids. Small molecules are typically not polymers with repeating units. In certain embodiments, a small molecule has a molecular weight of less than about 1500 g/mol. Also, small molecules typically have multiple carbon-carbon bonds and may have multiple stereocenters and functional groups.

"Solubility" refers to the amount of a substance that dissolves in a given volume of solvent at a specified temperature and pH, e.g., to form a saturated solution. Solubility may be determined, for example, using the shake-flask solubility method (ASTM: E 1148-02, Standard Test Method for Measurements of Aqueous Solubility, Book of Standards Volume 11.05). Solubility may be determined at a pH between 3.0 and 9.0, e.g., between 4.0 and 8.0, between 5.0 and 8.0, between 6.0 and 8.0, e.g., between 6.5 and 7.6, e.g., between 6.8-7.4, e.g., 7.0, or any intervening value of the foregoing ranges. Solubility may be tested at a temperature of between 20 and 40° C., e.g., approximately 25-37° C., e.g., approximately 37° C., or any intervening value of the foregoing ranges. For example, solubility may be determined at approximately pH 7.0-7.4 and approximately 37° C.

"Subject," as used herein, refers to an individual to whom an agent is to be delivered, e.g., for experimental, diagnostic, and/or therapeutic purposes. Preferred subjects are mammals, particularly domesticated mammals (e.g., dogs, cats, etc.), primates, or humans. A subject under the care of a physician or other health care provider may be referred to as a "patient."

"Pharmaceutical agent," also referred to as a "drug," is used herein to refer to an agent that is administered to a subject to treat a disease, disorder, or other clinically recognized condition that is harmful to the subject, or for prophylactic purposes, and has a clinically significant effect on the body to treat or prevent the disease, disorder, or condition. Therapeutic agents include, without limitation, agents listed in the United States Pharmacopeia (USP), *Goodman and Gilman's The Pharmacological Basis of Therapeutics*, 10$^{th}$ Ed., McGraw Hill, 2001; Katzung, B. (ed.) *Basic and Clinical Pharmacology*, McGraw-Hill/Appleton & Lange; 8th edition (Sep. 21, 2000); *Physician's Desk Reference* (Thomson Publishing), and/or *The Merck Manual of Diagnosis and Therapy*, 17$^{th}$ ed. (1999), or the 18$^{th}$ ed (2006) following its publication, Mark H. Beers and Robert Berkow (eds.), Merck Publishing Group, or, in the case of animals, *The Merck Veterinary Manual*, 9$^{th}$ ed., Kahn, C. A. (ed.), Merck Publishing Group, 2005.

"Viscosity" refers to a measurement of the thickness or resistance to flow of a liquid at a given temperature. Viscosity may be determined using a variety of methods and instruments known in the art. For example, a polymer is first weighed and then dissolved in an appropriate solvent. The solution and viscometer are placed in a constant temperature water bath. Thermal equilibrium is obtained within the solution. The liquid is then brought above the upper graduation mark on the viscometer. The time for the solution to flow from the upper to lower graduation marks is recorded. Viscosity of a solution comprising a polymer may be determined in accordance with ASTM Book of Standards, Practice for Dilute Solution Viscosity of Polymers (ASTM D2857), Volume 08.01, June 2005 or relevant ASTM standards for specific polymers. Solubility may be tested at a temperature of between 20 and 40° C., e.g., approximately 25-37° C., e.g., approximately 37° C., or any intervening value of the foregoing ranges. For example, solubility may be determined at approximately pH 7.0-7.4 and approximately 37° C.

"Elastic shear modulus" of a material is a mathematical description of a material's tendency to be deformed elastically (i.e., non-permanently) when a force is applied parallel to one of its surfaces while its opposite face experiences an opposing force (e.g., friction). Elastic shear modulus is calculated as the ratio of shear stress to shear strain. For example, if a force of 1 N is applied tangentially (on the xy plane) to a surface of an area of 1 m$^2$ and produces a change in the shape by 1% (strain=0.01) in the xy plane, then the elastic shear modulus of the material is 1/0.01=100 Pa.

DETAILED DESCRIPTION OF CERTAIN EMBODIMENTS OF THE INVENTION

The present invention stems from the recognition that the phonatory subepithelial soft tissue of the vocal folds must be pliable so that it can vibrate and produce sound. In a normal state, this is the superficial lamina propria (SLP). Based on this recognition, it has been discovered that injection of hydrogels into or underneath the phonatory epithelium can improve phonation in patients with stiff and/or scarred vocal folds. Hydrogels useful in this procedure typically have an elastic shear modulus ranging from approximately 15 Pa to approximately 35 Pa. The invention also provides novel hydrogels and compositions thereof useful in vocal cord repair as well as other soft tissues (e.g., skin, muscle, breast, bladder, intervertebral disks) of a patient.

Hydrogels

The present invention provides novel hydrogels for use in vocal cord repair, or other soft tissue repair or augmentation. Hydrogels are superabsorbent natural or synthetic polymers.

Hydrogels can contain up to 99% water by weight. It has been discovered that certain hydrogels are useful in vocal cord repair. The hydrogel may include one or more polymers. In certain embodiments, the hydrogel is a mixture of cross-linked and/or uncross-linked polymers. In particular, semi-interpenetrating networks of polymers that form hydrogels have been found to be useful in vocal cord repair. Interpenetrating networks of polymers that form hydrogels and one-component hydrogels have also been found to be useful in vocal cord repair. Furthermore, it has been discovered that hydrogels with an elastic shear modulus ranging from about 15 Pa to about 35 Pa are particularly useful for restoring the pliability of the phonatory mucosa of the vocal cords. In certain embodiments, the elastic shear modulus of the hydrogel ranges from about 20 Pa to about 30 Pa. In certain embodiments, the elastic shear modulus of the hydrogel is about 25 Pa.

In certain embodiments, the hydrogel only comprises one polymer. In certain other embodiments, the hydrogel comprises more than one polymer. In certain embodiments, the hydrogel comprises two polymers. In certain embodiments, the hydrogel comprises three, four, five, or more polymers. A mixture of polymers allows one to tune the desired characteristics of the hydrogel. Any polymer may be used in preparing a hydrogel. The polymers of the hydrogel may be natural or synthetic. Typically, the polymer(s) used in the hydrogel is at least somewhat water soluble. Examples of polymers useful in preparing hydrogels include, but are not limited to, polycarbonates (e.g. poly(1,3-dioxan-2one)), polyanhydrides (e.g. poly(sebacic anhydride)), polyhydroxyacids (e.g. poly(β-hydroxyalkanoate)), polypropylfumerates, polycaprolactones, polyamides (e.g. polycaprolactam, polylysine, peptides made with D-amino acids), polyacetals, polyethers, polyesters (e.g. polylactide, polyglycolide), poly(orthoesters), polycyanoacrylates, polyvinyl alcohols, polyurethanes, polyphosphazenes, polyacrylates, polymethacrylates, polyureas, polysaccharides (e.g., hyaluronic acid, dextran, alginate, cellulose), polyamines, and co-polymers thereof. Examples of natural polymers include proteins, peptides (e.g., elastin-like peptide, collagen-mimetic peptides, collagen-related peptides), polysaccharides (e.g., hyaluronic acid, methyl cellulose, dextran, alginate), and nucleic acids.

In certain embodiments, the hydrogel is prepared using a polyol. In certain embodiments, the hydrogel is prepared using a polyether (e.g., polyethylene glycol, polypropylene glycol, poly(tetramethylene ether) glycol). In certain embodiments, the hydrogel comprises polyethylene glycol. In certain embodiments, the hydrogel is prepared using a polyether and another type of polymer. In certain particular embodiments, the hydrogel is prepared using polyethylene glycol and another type of polymer. In certain embodiments, the hydrogel is prepared using a polyether and a protein. In certain embodiments, the hydrogel is prepared using a polyether and a polysaccharide. In certain embodiments, the hydrogel is prepared using a polyether and another polyether. In certain embodiments, the hydrogel is prepared using a polyether and a polyol. In certain embodiments, the hydrogel is prepared using at least two polyethers. In certain embodiments, the hydrogel is prepared using an acrylated version of polyethylene glycol and another type of polymer. In certain embodiments, the hydrogel is prepared using a diacrylated version of polyethylene glycol and another type of polymer. In certain particular embodiments, the hydrogel is prepared using poly(glycerol sebacate) and acrylated polyethylene glycol. In certain particular embodiments, the hydrogel is prepared using hyaluronic acid and acrylated polyethylene glycol. In certain particular embodiments, the hydrogel is prepared using methyl cellulose and acrylated polyethylene glycol. In certain particular embodiments, the hydrogel is prepared using dextran and acrylated polyethylene glycol. In certain particular embodiments, the hydrogel is prepared using alginate and acrylated polyethylene glycol. In certain particular embodiments, the hydrogel is prepared using polylysine and acrylated polyethylene glycol. In certain particular embodiments, the hydrogel is prepared using poly(glycerol sebacate) and polyethylene glycol-diacrylate. In certain particular embodiments, the hydrogel is prepared using hyaluronic acid and polyethylene glycol-diacrylate. In certain particular embodiments, the hydrogel is prepared using methyl cellulose and polyethylene glycol-diacrylate. In certain particular embodiments, the hydrogel is prepared using dextran and polyethylene glycol-diacrylate. In certain particular embodiments, the hydrogel is prepared using alginate and polyethylene glycol-diacrylate. In certain particular embodiments, the hydrogel is prepared using polylysine and polyethylene glycol-diacrylate.

In certain embodiments, the hydrogel is prepared using a cross-linkable peptide or protein and another type of polymer. In certain embodiments, the cross-linkable peptide is a cross-linkable version of elastin-like peptides (ELP), collagen-mimetic peptides (CMP), or collagen-related peptides (CRP). The peptide may include natural L-amino acids, unnatural D-amino acids, or a combination thereof. When a peptide is made from D-amino acids, the resulting peptide is typically less amenable to biodegradation, in particular enzymatic degradation. In certain embodiments, the cross-linkable peptide includes an acrylated version of the peptide. Other cross-linkable moieties as described herein may also be used. The cross-linkable peptide may be combined with any other polymer as described herein. In certain embodiments, the cross-linkable peptide is cross-linked in the presence of hyaluronic acid, collagen, gelatin, alginate, methyl cellulose, elastin, polylysine, or a derivative thereof. In certain embodiments, the hydrogel comprises a semi-interpenetrating network of acrylated ELP (D-peptide form) and hyaluronic acid. In certain embodiments, the hydrogel comprises a semi-interpenetrating network of acrylated ELP (L-peptide form) and hyaluronic acid. In certain embodiments, the hydrogel comprises a semi-interpenetrating network of acrylated ELP (D-peptide form) and collagen. In certain embodiments, the hydrogel comprises a semi-interpenetrating network of acrylated ELP (L-peptide form) and collagen. In certain embodiments, the hydrogel comprises a semi-interpenetrating network of acrylated ELP (D-peptide form) and polylysine. In certain embodiments, the hydrogel comprises a semi-interpenetrating network of acrylated ELP (L-peptide form) and polylysine. In certain embodiments, the hydrogel comprises a semi-interpenetrating network of acrylated ELP (D-peptide form) and dextran. In certain embodiments, the hydrogel comprises a semi-interpenetrating network of acrylated ELP (L-peptide form) and dextran. In certain embodiments, the hydrogel comprises a semi-interpenetrating network of acrylated ELP (D-peptide form) and alginate. In certain embodiments, the hydrogel comprises a semi-interpenetrating network of acrylated ELP (L-peptide form) and alginate. In certain embodiments, the hydrogel comprises a semi-interpenetrating network of acrylated polylysine and hyaluronic acid. In certain embodiments, the hydrogel comprises a semi-interpenetrating network of acrylated polylysine and dextran. In certain embodiments, the hydrogel comprises a semi-interpenetrating network of acrylated polylysine and alginate. In certain embodiments, the hydrogel comprises a semi-interpenetrating network of acrylated polylysine and elastin. In certain embodiments, the hydrogel comprises a semi-interpenetrating network of acrylated polylysine and collagen. In certain embodiments, the hydrogel comprises a semi-interpenetrating network of acrylated polylysine and polylysine. In certain embodiments, the hydrogel comprises a semi-interpenetrating network of acrylated polylysine and gelatin. In certain embodiments, the hydrogel will include only natural polymers. In certain embodiments, the hydrogel does not include polyethylene glycol or a derivative thereof.

In certain embodiments, the hydrogel is prepared using a cross-linkable polysaccharide and another type of polymer. In certain embodiments, the cross-linkable polysaccharide is a water soluble polysaccharide. In certain embodiments, the cross-linkable polysaccharide is a linear polysaccharide. In other embodiments, the cross-linkable polysaccharide is a branched polysaccharide. In certain embodiments, the hydrogel comprises a cross-linkable version of hyaluronic acid. In certain embodiments, the hydrogel comprises a cross-linkable version of methyl cellulose or other cellulose derivative. In certain embodiments, the hydrogel comprises a cross-linkable version of dextran. In certain embodiments, the hydrogel comprises a cross-linkable version of alginate. In certain embodiments, the cross-linkable polysaccharide is an acrylated version of a polysaccharide. Other cross-linkable moieties as described herein may also be used. The cross-linkable polysaccharide may be combined with any other polymer as described herein. In certain embodiments, the cross-linkable polysaccharide is cross-linked in the presence of hyaluronic acid, collagen, dextran, gelatin, polylysine, alginate, methyl cellulose, elastin, or a derivative thereof. In certain embodiments, the hydrogel comprises a semi-interpenetrating network of acrylated methyl cellulose and hyaluronic acid. In certain embodiments, the hydrogel comprises a semi-interpenetrating network of acrylated methyl cellulose and dextran. In certain embodiments, the hydrogel comprises a semi-interpenetrating network of acrylated methyl cellulose and alginate. In certain embodiments, the hydrogel comprises a semi-interpenetrating network of acrylated methyl cellulose and elastin. In certain embodiments, the hydrogel comprises a semi-interpenetrating network of acrylated methyl cellulose and collagen. In certain embodiments, the hydrogel comprises a semi-interpenetrating network of acrylated methyl cellulose and polylysine. In certain embodiments, the hydrogel comprises a semi-interpenetrating network of acrylated methyl cellulose and gelatin. In certain embodiments, the hydrogel comprises a semi-interpenetrating network of acrylated hyaluronic acid and hyaluronic acid. In certain embodiments, the hydrogel comprises a semi-interpenetrating network of acrylated hyaluronic acid and dextran. In certain embodiments, the hydrogel comprises a semi-interpenetrating network of acrylated hyaluronic acid and alginate. In certain embodiments, the hydrogel comprises a semi-interpenetrating network of acrylated hyaluronic acid and elastin. In certain embodiments, the hydrogel comprises a semi-interpenetrating network of acrylated hyaluronic acid and collagen. In certain embodiments, the hydrogel comprises a semi-interpenetrating network of acrylated hyaluronic acid and polylysine. In certain embodiments, the hydrogel comprises a semi-interpenetrating network of acrylated hyaluronic acid and gelatin. In certain embodiments, the acrylated hyaluronic acid is methacrylated hyaluronic acid. In certain embodiments, the hydrogel comprises a semi-interpenetrating network of acrylated dextran and hyaluronic acid. In certain embodiments, the hydrogel comprises a semi-interpenetrating network of acrylated dextran and dextran. In certain embodiments, the hydrogel comprises a semi-interpenetrating network of acrylated dextran and alginate. In certain embodiments, the hydrogel comprises a semi-interpenetrating network of acrylated dextran and elastin. In certain embodiments, the hydrogel comprises a semi-interpenetrating network of acrylated dextran and collagen. In certain embodiments, the hydrogel comprises a semi-interpenetrating network of acrylated dextran and polylysine. In certain embodiments, the hydrogel comprises a semi-interpenetrating network of acrylated dextran and gelatin. In certain embodiments, the hydrogel comprises a semi-interpenetrating network of acrylated alginate and hyaluronic acid. In certain embodiments, the hydrogel comprises a semi-interpenetrating network of acrylated alginate and dextran. In certain embodiments, the hydrogel comprises a semi-interpenetrating network of acrylated alginate and alginate. In certain embodiments, the hydrogel comprises a semi-interpenetrating network of acrylated alginate and elastin. In certain embodiments, the hydrogel comprises a semi-interpenetrating network of acrylated alginate and collagen. In certain embodiments, the hydrogel comprises a semi-interpenetrating network of acrylated alginate and polylysine. In certain embodiments, the hydrogel comprises a semi-interpenetrating network of acrylated alginate and gelatin. In certain embodiments, the hydrogel will include only natural polymers. In certain embodiments, the hydrogel includes only polysaccharides or derivatives of polysaccharides. In certain embodiments, the hydrogel does not include polyethylene glycol or a derivative thereof.

In certain embodiments, the hydrogel is prepared using a cross-linkable elastomeric polymer and another type of polymer. In certain embodiments, the hydrogel comprises a cross-linkable version of poly(glycerol sebacate) (PGS). In certain embodiments, the cross-linkable polysaccharide is an acrylated version of an elastomeric polymer. Other cross-linkable moieties as described herein may also be used. The cross-linkable elastomeric polymer may be combined with any other polymer as described herein. In certain embodiments, the cross-linkable elastomeric polymer is cross-linked in the presence of hyaluronic acid, collagen, gelatin, alginate, methyl cellulose, elastin, dextran, polylysine, or a derivative thereof. In certain embodiments, the cross-linkable elastomeric polymer is cross-linked in the presence of polyethylene glycol, poly(lactic acid), poly(glycolic acid), poly(lactic-co-glycolic acid), or a derivative thereof. In certain embodiments, the hydrogel comprises a semi-interpenetrating network of acrylated PGS and hyaluronic acid. In certain embodiments, the hydrogel comprises a semi-interpenetrating network of acrylated PGS and methyl cellulose. In certain embodiments, the hydrogel comprises a semi-interpenetrating network of acrylated PGS and elastin. In certain embodiments, the hydrogel comprises a semi-interpenetrating network of acrylated PGS and collagen. In certain embodiments, the hydrogel comprises a semi-interpenetrating network of acrylated PGS and gelatin. In certain embodiments, the hydrogel comprises a semi-interpenetrating network of acrylated PGS and dextran. In certain embodiments, the hydrogel comprises a semi-interpenetrating network of acrylated PGS and alginate. In certain embodiments, the hydrogel comprises a semi-interpenetrating network of acrylated PGS and polylysine. In certain embodiments, the hydrogel comprises a semi-interpenetrating network of acrylated PGS and polyethylene glycol (PEG). In certain embodiments, the hydrogel will include only natural polymers. In certain embodiments, the hydrogel does not include polyethylene glycol or a derivative thereof.

In certain embodiments, the hydrogel is a semi-interpenetrating network of polymers formed when a polymer is crosslinked with itself in the presence of a non-crosslinkable polymer. In certain embodiments, the crosslinkable polymer is water soluble. In certain embodiments, the non-crosslinkable polymer is water soluble. The water-soluble polymer typically has a minimum solubility of at least approximately 0.1 g of polymer per liter of water. In certain embodiments, the solubility of the polymer in water is at least approximately 0.5 g of polymer per liter of water. In certain embodiments, the solubility of the polymer in water is at least approximately 1 g of polymer per liter of water. In certain embodiments, the solubility of the polymer in water is at least approximately 5 g of polymer per liter of water. In certain embodiments, the solubility of the polymer in water is at least approximately 10 g of polymer per liter of water. The hydrogel may also include other polymers, which may be water soluble or not. Any of the polymers described herein may be used to prepare semi-interpenetrating networks of polymers. In certain embodiments, a polyether is used in the preparation of the semi-interpenetrating network of polymers. In certain embodiments, a polymer is modified to make it suitable for cross-linking. For example, functional groups suitable for cross-linking (e.g., acrylate moieties, vinyl moieties, alkenyl moieties, alkynyl moieties, methacrylate moieties, cyanoacrylate moieties) may be added to the polymer.

The crosslinkable polymer component of the hydrogel may be any synthetic or natural polymer which is capable of being cross-linked. In certain embodiments, the cross-linkable polymer is a synthetic polymer. In certain embodiments, the crosslinkable polymer is a natural polymer such as a protein or carbohydrate. The polymer typically will include or may be modified to include functional groups suitable for cross-linking such as acrylates, methacrylates, alkenes, alkynes, carboxylic acids, amines, aldehydes, halides, azides, esters, thiols, diazirines, carbodiimides, imidoesters, azenes, strained rings such as epoxides or aziridines, etc. In certain embodiments, the polymer is an acrylated polyethylene glycol. For example, polyethylene glycol diacrylate, polyethylene glycol triacrylate, etc. may be used as the crosslinkable polymer in the hydrogel. Other polymers besides polyethylene glycol may form the backbone of the polymer. Other exemplary polymer backbones include, but are not limited to, polyesters, polyamines, polyethers, polyamides, polyureas, polyanhydrides, polyhydroxyacids, polypropylfumarates, polycaprolactones, polyacetals, poly(orthoesters), polyvinyl alcohol, polyurethanes, polyphosphazenes, and polycarbonates. In certain embodiments, the polymer backbone is polypropylene glycol. In certain embodiments, the polymer backbone is polybutylene glycol. In certain embodiments, the polymer is methacrylated rather than acrylated. In certain embodiments, the polymer is cyanoacrylated. In other embodiments, the polymer comprises vinyl moieties rather than acrylate or methacrylate moieties. In certain embodiments, the polymer comprises azide moieties. In certain embodiments, the polymer comprises strained rings. In certain embodiments, the polymer comprises an epoxide moiety. In certain embodiments, the polymer comprises an aziridine moiety. In certain embodiments, the polymer comprises an amine. In certain embodiments, the polymer comprises an aldehyde. In certain embodiments, the polymer comprises a halogen. In certain embodiments, the polymer comprises an alkenyl moiety. In certain embodiments, the polymer comprises an alkynyl moiety. In certain embodiments, the polymer comprises a carboxylic acid. In certain embodiments, the polymer comprises an ester. In certain embodiments, the polymer comprises a thiol. In certain embodiments, the polymer comprises a diazirine. In certain embodiments, the polymer comprises a carbodiimide. In certain embodiments, the polymer comprises an imidoester. In certain embodiments, the polymer comprises an azene moiety. In certain embodiments, the polymer comprises a nitrene moiety.

The non-crosslinkable polymer component of the hydrogel may also be synthetic or natural. Typically, the non-crosslinkable polymer component of the hydrogel is a water-soluble polymer. In certain embodiments, the non-crosslinkable polymer is a synthetic polymer. In other embodiments, the non-crosslinkable polymer is a natural polymer. Exemplary non-crosslinkable, water soluble polymers include, but are not limited to, polyethers, polypeptides (e.g., polylysine, polyserine, polythreonine, polyglutamate, polyaspartate, polyhistidine, polyarginine), polysaccharides (e.g., alginates, dextran, cellulose, hyaluronic acid), polyamides, proteins (e.g., gelatin, elastin), and derivatives thereof. In certain embodiments, the non-crosslinkable polymer is analogous to the crosslinkable polymer, for example, a non-acrylated polymer (e.g., polyethylene glycol) versus an acrylated polymer (e.g., polyethylene glycol diacrylate).

The physicochemical properties of the hydrogel may be varied by changing the portion of crosslinkable polymer as compared to non-crosslinkable polymer, molecular weights of either or both polymers, concentration of polymer, and extent of cross-linking.

The molecular weight of either polymer may range from approximately 2,000 g/mol up to approximately 600,000 g/mol. In certain embodiments, the molecular weight of the polymer ranges from approximately 5,000 g/mol to approximately 30,000 g/mol. In certain embodiments, the molecular weight of the polymer ranges from approximately 5,000 g/mol to approximately 10,000 g/mol. In certain embodiments, the molecular weight of the polymer ranges from approximately 10,000 g/mol to approximately 15,000 g/mol. In certain embodiments, the molecular weight of the polymer ranges from approximately 10,000 g/mol to approximately 20,000 g/mol. In certain embodiments, the molecular weight of the polymer ranges from approximately 20,000 g/mol to approximately 30,000 g/mol. In certain embodiments, the molecular weight of the polymer ranges from approximately 30,000 g/mol to approximately 40,000 g/mol. In certain embodiments, the molecular weight of the polymer ranges from approximately 40,000 g/mol to approximately 50,000 g/mol. In certain embodiments, the molecular weight of the crosslinkable polymer before cross-linking is approximately 5,000 g/mol, approximately 10,000 g/mol, approximately 15,000 g/mol, approximately 20,000 g/mol, approximately 25,000 g/mol, approximately 30,000 g/mol, approximately 35,000 g/mol, approximately 40,000 g/mol, approximately 45,000 g/mol, and approximately 50,000 g/mol. In certain embodiments, the molecular weight of the non-crosslinkable polymer is approximately 5,000 g/mol, approximately 10,000 g/mol, approximately 15,000 g/mol, approximately 20,000 g/mol, approximately 25,000 g/mol, approximately 30,000 g/mol, approximately 35,000 g/mol, approximately 40,000 g/mol, approximately 45,000 g/mol, and approximately 50,000 g/mol. In certain embodiments, the molecular weight of the polymer ranges from approximately 50,000 g/mol to approximately 100,000 g/mol. In certain embodiments, the molecular weight of the polymer ranges from approximately 100,000 g/mol to approximately 200,000 g/mol. In certain embodiments, the molecular weight of the polymer ranges from approximately 200,000 g/mol to approximately 300,000 g/mol. In certain embodiments, the molecular weight of the polymer is approximately 250,000 g/mol. In certain embodiments, the molecular weight of the polymer ranges from approximately 300,000 g/mol to approximately 400,000 g/mol. In certain embodiments, the molecular weight of the polymer ranges from approximately 400,000 g/mol to approximately 500,000 g/mol. In certain embodiments, the molecular weight of the polymer ranges from approximately 500,000 g/mol to approximately 600,000 g/mol.

Any ratio of crosslinkable to non-crosslinkable polymer may be used in the inventive hydrogels. In certain embodiments, a nearly equal portion of each polymer component is used to prepare the hydrogel. In certain embodiments, the amount of one of the polymers is greater than the other. In certain embodiments, the amount of the non-crosslinkable polymer is greater than the amount of the crosslinkable polymer. In certain embodiments, the ratio of non-crosslinkable polymer to crosslinkable polymer is about 10:90, about 20:80, about 30:70, about 40:60, about 50:50, about 60:40, about 70:30, about 80:20, or about 90:10. In certain particular embodiments, the ratio of non-crosslinkable polymer to crosslinkable polymer is about 70:30. In certain particular embodiments, the ratio of non-crosslinkable polymer to crosslinkable polymer is about 69:31. In certain particular embodiments, the ratio of non-crosslinkable polymer to crosslinkable polymer is about 71:29. In certain particular embodiments, the ratio of non-crosslinkable polymer to crosslinkable polymer is about 72:28. In certain particular embodiments, the ratio of non-crosslinkable polymer to crosslinkable polymer is about 65:35. In certain embodiments, the percentage of crosslinkable polymer in the hydrogel ranges from approximately 10% to approximately 50%. In certain embodiments, the percentage of crosslinkable polymer in the hydrogel ranges from approximately 20% to approximately 40%. In certain embodiments, the percentage of crosslinkable polymer in the hydrogel ranges from approximately 25% to approximately 35%. In certain embodiments, the percentage of crosslinkable polymer in the hydrogel is approximately 25%. In certain embodiments, the percentage of crosslinkable polymer in the hydrogel is approximately 30%. In certain embodiments, the percentage of crosslinkable polymer in the hydrogel is approximately 35%. In certain embodiments, the percentage of crosslinkable polymer in the hydrogel is approximately 40%. In certain embodiments, the percentage of crosslinkable polymer in the hydrogel is approximately 25%, approximately 26%, approximately 27%, approximately 28%, approximately 29%, approximately 30%, approximately 31%, approximately 32%, approximately 33%, approximately 34%, or approximately 35%.

The crosslinkable polymer of the semi-interpenetrating network of polymer is cross-linked via a free radical mediated process. The two or more polymeric components are mixed together in the desired proportion in the hydrogel, and a cross-linking reaction is initiated to crosslink the cross-linkable polymer. In certain embodiments, the polymer is cross-linked using a free radical initiator. The initiator may be a thermal initiator or a photoinitiator. In certain embodiments, the polymer is cross-linked by photo-induced cross-linking (e.g., UV light, visible light, IR light). In certain embodiments, the light is centered at approximately 365 nm. In other embodiments, the polymer is cross-linked by heat (e.g., 30-200° C.). In other embodiments, the polymer is cross-linked using a biological or chemical catalyst. The cross-linking process is performed under conditions suitable to yield the desired properties of the resulting hydrogel. For example, the extent of cross-linking may be controlled by the time of the reaction, the amount/concentration of initiator, the polymer starting material, the initiator, the frequency of the light used to effect the cross-linking, additives, temperature of the reaction, solvent used, concentration of polymer starting material, oxygen inhibition, water inhibition, etc.

Typically, the initiator decomposes upon heating or exposure to a certain wavelength of light to yield two free radicals that initiate the cross-linking reaction. The initiator may work in a variety of organic solvents, water, or aqueous solutions. Organic solvents that can be used include acetone, ethers, bezene, THF, toluene, hexanes, DMSO, DMF, etc. In certain embodiments, the cross-linking reaction is performed in water or an aqueous solution. In certain particular embodiments, the cross-linking reaction is performed in phosphate-buffered saline solution. The aqueous solution may be acidic or basic.

The initiator is typically chosen based on a variety of concerns including the structure of the polymer, the desired cross-linked material to be produced, the extent of cross-linking, the subsequent use of the material, etc. These and other concerns may be taken into account by one of skill in the art choosing the thermal initiator to be used. The initiator may be obtained from a commercial source such as Sigma-Aldrich, Ciba-Geigy, Sartomer, etc. The initiator may also be prepared synthetically.

In certain embodiments, the initiator is a thermal initiator. Any thermal initiator may be used in the cross-linking reaction. In certain embodiments, the thermal initiator is designed to work at a temperature ranging from 30° C. to 200° C. In certain embodiments, the initiator is designed to work at a temperature ranging from 50° C. to 170° C. In other embodiments, the initiator is designed to work at a temperature ranging from 50° C. to 100° C. In certain embodiments, the initiator is designed to work at a temperature ranging from 100° C. to 170° C. In certain particular embodiments, the initiator is designed to work at approximately 50, 60, 70, 80, 90, 100, 110, 120, 130, 140, 150, 160, or 170° C. The thermal initiators may be peroxides, peracids, peracetates, persulfates, etc. Exemplary thermal initiators include tert-amyl peroxybenzoate; 4,4-azobis (4-cyanovaleric acid); 1,1'-azobis (cyclohexanecarbonitrile); 2,2'-azobisisobutyronitrile (AIBN); benzoyl peroxide; 2,2-bis (tert-butylperoxy) butane; 1,1-bis(tert-butylperoxy)cyclohexane; 2,5-bis (tert-butylperoxy)-2,5-dimethylhexane; 2,5-bis(tert-butylperoxy)-2,5-dimethyl-3-hexyne; bis(1-(tert-butylperoxy)-1-methylethyl)benzene; 1,1-bis (tert-butylperoxy)-3,3,5-trimethylcyclohexane; tert-butyl hydroperoxide; tert-butyl peracetate; tert-butyl peroxide; tert-butyl peroxybenzoate; tert-butylperoxy isopropyl carbonate; cumene hydroperoxide; cyclohexanone peroxide; dicumyl peroxide; lauroyl peroxide; 2,4-pentanedione peroxide; peracetic acid; and potassium persulfate. In certain embodiments, a combination of thermal initiators is used.

In other embodiments, the initiator is a photoinitiator. Photoinitiators produce reactive free radical species that initiate the cross-linking of the cross-linkable component of the hydrogel. Any photoinitiator may be used in the cross-linking reaction. Photoinitiated polymerizations and photoinitiators are discussed in detail in Rabek, *Mechanisms of Photophysical Processes and Photochemical Reactions in Polymers*, New York: Wiley & Sons, 1987; Fouassier, *Photoinitiation, Photopolymerization, and Photocuring*, Cincinnati, Ohio: Hanser/Gardner; Fisher et al., "Photoinitiated Polymerization of Biomaterials" Annu. Rev. Mater. Res. 31:171-81, 2001; incorporated herein by reference. The photoinitiator may be designed to produce free radicals at any wavelength of light. In certain embodiments, the photoinitiator is designed to work using UV light (200-400 nm). In certain embodiments, long UV rays are used. In other embodiments, short UV rays are used. In other embodiments, the photoinitiator is designed to work using visible light (400-800 nm). In certain embodiments, the photoinitiator is designed to work using blue light (420-500 nm). In yet other embodiments, the photinitiator is designed to work using IR light (800-2500 nm). In certain embodiments, the photoinitiator is a peroxide (e.g., ROOR'). In other embodiments, the photoinitiator is a ketone (e.g., RCOR'). In other embodiments, the compound is an azo compound (e.g., compounds with a —N=N— group). In certain embodiments, the photoinitiator is an acylphosphineoxide. In other embodiments, the photoinitiator is a sulfur-containing compound. In still other embodiments, the initiator is a quinone. Exemplary photoinitiators include acetophenone; anisoin; anthraquinone; anthraquinone-2-sulfonic acid, sodium salt monohydrate; (benzene) tricarbonylchromium; benzin; benzoin; benzoin ethyl ether; benzoin isobutyl ether; benzoin methyl ether; benzophenone; benzophenone/1-hydroxycyclohexyl phenyl ketone; 3,3',4,4'-benzophenonetetracarboxylic dianhydride; 4-benzoylbiphenyl; 2-benzyl-2-(dimethylamino)-4'-morpholinobutyrophenone; 4,4'-bis(diethylamino)benzophenone; 4,4'-bis(dimethylamino) benzophenone; camphorquinone; 2-chlorothioxanthen-9-one; (cumene)cyclopentadienyliron(II) hexafluorophosphate; dibenzosuberenone; 2,2-diethoxyacetophenone; 4,4'-dihydroxybenzophenone; 2,2-dimethoxy-2-phenylacetophenone; 4-(dimethylamino)benzophenone; 4,4'-dimethylbenzil; 2,5-dimethylbenzophenone; 3,4-dimethylbenzophenone; diphenyl(2,4,6-trimethylbenzoyl)phosphine oxide/2-hydroxy-2-methylpropiophenone; 4'-ethoxyacetophenone; 2-ethylanthraquinone; ferrocene; 3'-hydroxyacetophenone; 4'-hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methylbenzophenone; methybenzoylformate; 2-methyl-4'-(methylthio)-2-morpholinopropiophenone; phenanthrenequinone; 4'-phenoxyacetophenone; thioxanthen-9-one; triarylsulfonium hexafluoroantimonate salts; triarylsulfonium hexafluorophosphate salts; hydrogen peroxide; benzoyl peroxide; benzoin; 2,2-dimethoxy-2-phenylacetophenone; dibenzoyl disulphides; diphenyldithiocarbonate; 2,2'-azobisisobutyronitrile (AIBN); camphorquinone (CQ); eosin; dimethylaminobenzoate (DMAB); dimethoxy-2-phenyl-acetophenone (DMPA); Quanta-cure ITX photosensitizer (Biddle Sawyer); Irgacure 907 (Ciba Geigy); Irgacure 651 (Ciba Geigy); Irgacure 2959 (Ciba Geigy); Darocur 2959 (Ciba Geigy); ethyl-4-N,N-dimethylaminobenzoate (4EDMAB); 1-[-(4-benzoylphenylsulfanyl)phenyl]-2-methyl-2-(4-methylphenylsulfonyl) propan-1-one; 1-hydroxy-cyclohexyl-phenyl-ketone; 2,4,6-trimethylbenzoyldiphenylphosphine oxide; 2-ethylhexyl-4-dimethylaminobenzoate; 2-hydroxy-2-methyl-1-phenyl-1-propanone; 65% (oligo[2-hydroxy-2-methyl-1-[4-(1-methylvinyl)phenyl]propanone] and 35% propoxylated glyceryl triacrylate; benzil dimethyl ketal; benzophenone; blend of benzophenone and a-hydroxy-cyclohexyl-phenyl-ketone; blend of Esacure KIP150 and Esacure TZT; blend of Esacure KIP150 and Esacure TZT; blend of Esacure KIP150 and TPGDA; blend of phosphine oxide, Esacure KIP150 and Esacure TZT; difunctional a-hydroxy ketone; ethyl 4-(dimethylamino) benzoate; isopropyl thioxanthone; liquid blend of 4-methylbenzophenone and benzophenone; oligo(2-hydroxy-2 methyl-1-4 (1-methylvinyl)phenyl propanone (emulsion); oligo(2-hydroxy-2-methyl-1-4 (1-methylvinyl) phenyl propanone and 2-hydroxy-2-methyl-1-phenyl-1-propanone (monomeric); oligo (2-hydroxy-2-methyl-1-4 (1-methylvinyl) phenyl propanone and 2-hydroxy-2-methyl-1-phenyl-1-propanone (polymeric); trimethylbenzophenone and methylbenzophenone; and water emulsion of 2,4,6-trimethylbenzoylphosphine oxide, alpha hydroxyketone, trimethylbenzophenone, and 4-methyl benzophenone. In certain embodiments, the photoinitiator is Irgacure 2959. In certain embodiments, a combination of photoinitiators is used.

The hydrogel may be optionally purified and/or otherwise processed after it has been prepared. In certain embodiments, after the hydrogel is created, it is sheared to create a hydrogel composition of the desired elastic shear modulus. Shearing is typically done by forcing the hydrogel through a narrowed opening. In certain embodiments, smaller and smaller openings may be used. In certain embodiments, the hydrogel is forced through a series of needles with smaller and smaller bores. For example, the hydrogel may be passed successively through 16 gauge, 18 gauge, 20 gauge, and 22 gauge needles. In certain embodiments, a syringe-like device that can contain a larger volume is used. In other embodiments, ultrasonic and/or mechanical shearing methods may be used. In certain embodiments, a homogenizer is used. In certain embodiments, a microfluidizer is used. The hydrogel is typically processed until the desired elastic shear modulus of the material is achieved. In certain embodiments, the elastic shear modulus ranges from approximately 15 Pa to approximately 35 Pa. In certain embodiments, the elastic shear modulus ranges from approximately 20 Pa to approximately 30 Pa. In certain embodiments, the elastic shear modulus is approximately 21 Pa. In certain embodiments, the elastic shear modulus is approximately 22 Pa. In certain embodiments, the elastic shear modulus is approximately 23 Pa. In certain embodiments, the elastic shear modulus is approximately 24 Pa. In certain embodiments, the elastic shear modulus is approximately 25 Pa. In certain embodiments, the elastic shear modulus is approximately 26 Pa.

In certain embodiments, the hydrogel is a composition comprising acrylated polyethylene glycol and polyethylene glycol. In certain particular embodiments, the hydrogel is a composition comprising polyethylene glycol diacrylate and polyethylene glycol. In certain embodiments, the molecular weight of the polyethylene glycol diacrylate is approximately 10,000 g/mol. In certain embodiments, the molecular weight of the polyethylene glycol is approximately 10,000 g/mol. Seven parts of a 10% solution of the non-crosslinkable polymer is mixed with three parts of a 10% solution of the crosslinkable polymer, and the resulting composition is cross-linked using a photoinitiator and UV light. In certain embodiments, the photoinitiator Irgacure 2959 (Ciba Specialty Chemicals, Tarrytown, N.J.) is used in the photopolymerization reaction. The intensity of the UV light ranges from about 1 mW/cm$^2$ to about 20 mW/cm$^2$. In certain embodiments, the intensity of the UV light is about 10 mW/cm$^2$. The resulting hydrogel is sheared by passing it through needles of decreasing bore size (e.g., 16 gauge, 18 gauge, 20 gauge, and 22 gauge needles). In certain embodiments, the hydrogel is passed through each size of needle twice before using a smaller needle.

In certain embodiments, the hydrogel is a composition comprising acrylated polyethylene glycol and hyaluronic acid. In certain particular embodiments, the hydrogel is a composition comprising polyethylene glycol diacrylate and hyaluronic acid. In certain embodiments, the molecular weight of the polyethylene glycol diacrylate is approximately 10,000 g/mol. In certain embodiments, the molecular weight of the hyaluronic acid is approximately 560,000 g/mol. Seventy-three parts of a 1 mg/mL solution of the hyaluronic acid is mixed with twenty-seven parts of a 100 mg/mL of the crosslinkable polymer, and the resulting composition is cross-linked using a photoinitiator and UV light. In certain embodiments, the photoinitiator Irgacure 2959 (Ciba Specialty Chemicals, Tarrytown, N.J.) is used in the photopolymerization reaction. The intensity of the UV light ranges from about 0.5 mW/cm$^2$ to about 20 mW/cm$^2$. In certain embodiments, the intensity of the UV light ranges from about 1 mW/cm$^2$ to about 5 mW/cm$^2$. In certain embodiments, the intensity of the UV light ranges from about 5 mW/cm$^2$ to about 10 mW/cm$^2$. In certain embodiments, the intensity of the UV light is about 1 mW/cm$^2$. In certain embodiments, the intensity of the UV light is about 2 mW/cm$^2$. In certain embodiments, the intensity of the UV light is about 5 mW/cm$^2$. In certain embodiments, the intensity of the UV light is about 10 mW/cm$^2$. The resulting hydrogel is sheared by passing it through needles of decreasing bore size (e.g., 16 gauge, 18 gauge, 20 gauge, and 22 gauge needles). In certain embodiments, the hydrogel is passed through each size of needle twice before using a smaller needle.

In certain embodiments, the hydrogel is a composition comprising acrylated polyethylene glycol and dextran. In certain particular embodiments, the hydrogel is a composition comprising polyethylene glycol diacrylate and dextran. In certain embodiments, the molecular weight of the polyethylene glycol diacrylate is approximately 10,000 g/mol. In certain embodiments, the molecular weight of the dextran is approximately 200,000 g/mol. Seven parts of a 20 mg/mL solution of the dextran is mixed with three parts of a 100 mg/mL of the crosslinkable polymer, and the resulting composition is cross-linked using a photoinitiator and UV light. In certain embodiments, the photoinitiator Irgacure 2959 (Ciba Specialty Chemicals, Tarrytown, N.J.) is used in the photopolymerization reaction. The intensity of the UV light ranges from about 1 mW/cm$^2$ to about 20 mW/cm$^2$. In certain embodiments, the intensity of the UV light is about 10 mW/cm$^2$. The resulting hydrogel is sheared by passing it through needles of decreasing bore size (e.g., 16 gauge, 18 gauge, 20 gauge, and 22 gauge needles). In certain embodiments, the hydrogel is passed through each size of needle twice before using a smaller needle.

The hydrogel useful in the present invention typically do not degrade in vivo or breakdown slowly. The lack of biodegradability is predominantly useful to prevent the hydrogel having to be re-injected into the vocal folds or other area repeatedly. Typically, such injections should be repeated only once per month, once every 2-3 months, once every 6 months, or once every year. The longer the time between injections of the hydrogel the better.

The hydrogel may be combined with other therapeutically active agents and/or pharmaceutically acceptable excipients to form a composition useful for vocal cord repair or other soft tissue repair or augmentation.

In some embodiments, the present invention provides for compositions comprising hydrogels as described herein. Such compositions may optionally comprise one or more additional biologically active agents. In some embodiments, inventive compositions are administered to humans.

Although the descriptions of hydrogel compositions provided herein are principally directed to compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions of the invention is contemplated include, but are not limited to, humans and/or other primates; mammals, including mammals such as cattle, pigs, horses, sheep, cats, ferrets, and/or canines.

The formulations of the pharmaceutical compositions described herein may be prepared by any method known or hereafter developed in the art of pharmaceutics. In general, such preparatory methods include the step of bringing the hydrogel into association with one or more excipients and/or one or more other accessory ingredients, and then, if necessary and/or desirable, shaping, and/or packaging the product into a desired single- or multi-dose unit.

The relative amounts of the hydrogel, the pharmaceutically acceptable excipient(s), and/or any additional ingredients in a pharmaceutical composition of the invention will vary, depending upon the identity, size, and/or condition of the subject. By way of example, the composition may comprise between 1% and 99% (w/w) of the hydrogel.

Pharmaceutical formulations of the present invention may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro, (Lippincott, Williams & Wilkins, Baltimore, Md., 2006; incorporated herein by reference) discloses various excipients used in formulating pharmaceutical compositions and known techniques for the preparation thereof. Except insofar as any conventional excipient is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of the hydrogel compositions include, but are not limited to, inert diluents, dispersing agents, surface active agents and/or emulsifiers, disintegrating agents, preservatives, buffering agents, lubricating agents, and/or oils. Such excipients may optionally be included in the inventive formulations. Excipients such as coloring agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof Exemplary dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween® 20], polyoxyethylene sorbitan [Tween® 60], polyoxyethylene sorbitan monooleate [Tween® 80], sorbitan monopalmitate [Span® 40], sorbitan monostearate [Span® 60], sorbitan tristearate [Span® 65], glyceryl monooleate, sorbitan monooleate [Span® 80]), polyoxyethylene esters (e.g. polyoxyethylene monostearate [Myrj® 45], polyoxyethylene hydrogenated castor oil, polyethoxylated castor oil, polyoxymethylene stearate, and Solutol), sucrose fatty acid esters, polyethylene glycol fatty acid esters (e.g. Cremophor®), polyoxyethylene ethers, (e.g. polyoxyethylene lauryl ether [Brij® 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus®, Phenonip®, methylparaben, Germall 115, Germaben II, Neolone™, Kathon™, and Euxyl®. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for parenteral administration include, but are not limited to, pharmaceutically acceptable emulsions, microemulsions, solutions, suspensions, syrups, and elixirs. In addition to the hydrogel, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In certain embodiments, the hydrogel of the invention is mixed with solubilizing agents such as Cremophor®, alcohols, oils, modified oils, glycols, polysorbates, cyclodextrins, polymers, and combinations thereof.

Injectable formulations, for example, sterile injectable aqueous or oleaginous suspensions, may be formulated according to the known art using suitable dispersing or wetting agents and suspending agents. A sterile injectable preparation may be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

General considerations in the formulation and/or manufacture of pharmaceutical agents may be found, for example, in *Remington: The Science and Practice of Pharmacy* 21$^{st}$ ed., Lippincott Williams & Wilkins, 2005.

The inventive hydrogel may be combined with one or more biologically active agents. In certain embodiments, the hydrogel is combined with a pharmaceutical agent. In certain embodiments, the hydrogel is combined with an anti-inflammatory agent. In certain embodiments, the hydrogel is combined with an anti-fibrotic agent. In certain embodiments, the hydrogel is combined with an anti-proliferative agent. In certain embodiments, the hydrogel is combined with an antibiotic. In certain embodiments, the hydrogel is combined with a protein or peptide. In certain embodiments, the hydrogel is combined with a growth factor. In certain embodiments, the hydrogel is combined with cells. In certain embodiments, the hydrogel is combined with autologous cells. In certain embodiments, the hydrogel is combined with stem cells. In certain embodiments, the hydrogel is combined with a liquid excipient for administering the hydrogel. In certain embodiments, the excipient is an aqueous solution. In certain embodiments, the excipient is a buffered aqueous solution. In certain embodiments, the excipient is phosphate-buffered saline solution. In certain embodiments, the excipient is isotonic with extracellular fluid.

Uses

The invention further provides methods of injecting polymeric hydrogels or compositions thereof into the vocal cords or just under the phonatory epithelium of the vocal cords to restore the pliability of scarred vocal folds. In certain embodiments, the hydrogel is injected in the lost subepithelial superficial lamina propria layer of the mucosa. The inventive hydrogels may also be used to repair or augment other soft tissues. In certain embodiments, the hydrogel is used to augment the bladder neck for urinary incontinence. In other embodiments, the hydrogel is used as dermal fillers, breast implants, intervertebral disks, muscle-mass, and joint fluid.

In the setting of vocal cord repair, the hydrogel or other material is injected into the residual superficial lamina propria or just under phonatory epithelium. As described herein, it has been discovered that hydrogels with an elastic shear modulus ranging from approximately 20 Pa to approximately 30 Pa are particularly useful in restoring the pliability of the phonatory mucosa. One or both vocal folds may be treated using the inventive technique. In certain embodiments, approximately 0.1 mL to approximately 5 mL of hydrogel composition is injected into the vocal fold. The hydrogel is injected into the vocal folds using a very thin gauge needle (e.g., 25-30 gauge).

The hydrogel may last from weeks to months in the subepithelial region or superficial lamina propria (SLP) of the vocal cords. As needed, the procedure may be repeated in order to restore the pliability of the vocal cords, thereby restoring the patient's voice. The frequency of treatment will depend on the patient and the hydrogel being injected. In the case, of a patient with vocal fold paralysis, the treating physician may desire that the implant degrade after approximately 6 months to provide voice function while allowing for natural vocal nerve regeneration.

Other materials with similar properties (e.g., elastic shear modulus of approximately 15 Pa to approximately 35 Pa) to those of the hydrogels described herein may also be used in vocal cord or soft tissue repair or augmentation. Typically the material is a soft gel-like material. Such materials may be used alone or in conjunction with the hydrogels described herein. Exemplary materials for use in the inventive methods may include viscosupplements and dermal fillers. In certain embodiments, the material used comprises hyaluronic acid or a salt thereof. In certain embodiments, the viscosupplement is HYALGAN® (sodium hyaluronate), SYNVISC® (Hylan G-F 20), or ORTHOVISC® (high molecular weight hyaluronan). Other viscosupplements may be used. In certain embodiments, the dermal filler is RESTYLANE® (hyaluronic acid), PERLANE® (hyaluronic acid), HYLAFORM® (stabilized hyaluronic acid), or RADIESSE® (calcium hydroxylapatite microspheres in a water-based gel). Other dermal fillers may be used.

Kits

The invention also provides packages or kits, comprising one or more hydrogels or hydrogel components as described herein in a container. For example, the container may include a hydrogel composition ready for use in a patient. Or the containers may contain the components of the hydrogel (e.g., crosslinkable polymer, non-crosslinkable polymer) which must be mixed and cross-linked to form the hydrogel. The package can also include a notice associated with the container, typically in a form prescribed by a government agency regulating the manufacture, use, or sale of medical devices and/or pharmaceuticals, whereby the notice is reflective of approval by the agency of the compositions, for human or veterinary administration to treat vocal cord disease or other soft tissue repair or augmentation. Instructions for the use of the hydrogel composition may also be included. Such instructions may include information relating to administration of the hydrogel to a patient. In particular, the instructions may include information regarding the injection of the hydrogel into the vocal cords of patient.

In certain embodiments of the invention the kit will include multiple individual containers, each containing a component of the hydrogel. For example, a first container may contain a crosslinkable polymer, and a second container may contain a non-crosslinkable polymer. The cross-linking initiator may be provided in yet a third container. The polymers may be provided in predetermined amounts such that when mixed with each other in solution in the presence of an initiator they form a hydrogel having the desired characteristics. The package may also include one or more containers containing biologically active agent(s) to be included in the hydrogel prior to administration.

The package may include a device or receptacle for preparation of a hydrogel composition. The device may be, e.g., a measuring or mixing device.

The package may also optionally include a device for administering a hydrogel composition of the invention. Exemplary devices include specialized syringes, needles, and catheters that are compatible with a variety of laryngoscope designs.

The components of the kit may be provided in a single larger container, e.g., a plastic or styrofoam box, in relatively close confinement. Typically, the kit is conveniently packaged for use by a health care professional. In certain embodiments, the components of the kit are sterilely packaged for use in a sterile environment such as an operating room or physician's office.

EXAMPLES

Example 1

Preparation of Hydrogels for Injection into a Scarred Vocal Fold

Semi-interpenetrating networks technology was used to make the hydrogels of this Example. This process involves using a cross-linkable polymer (X) that is polymerized in the presence of a non-crosslinkable polymer (Y). The physicochemical properties of the gels were controlled by independently varying i) the fraction (f) of X in the solution; ii) the concentrations ($C_X$ and $C_Y$) of the components; and iii) the molecular weights ($M_X$ and $M_Y$) of the components of the hydrogel. All the polymers used to form the hydrogels in this Example were water-soluble. Photopolymerization using UV light (centered at 365 nm) was carried out using Irgacure 2959 (Ciba Specialty Chemicals, Tarrytown, N.Y.) as the photoinitiator. The description given below outlines the detailed protocol for preparing certain exemplary hydrogels where, X=Polyethylene Glycol Diacrylate (PEG-DA) obtained from SunBio Inc.
Y=Polyethylene Glycol (PEG)
$C_X$=100 mg/mL (10% w/v) before mixing
$C_Y$=100 mg/mL (10% w/v) before mixing
$M_X$=10,000 (10 kDa)
$M_Y$=10,000 (10 kDa)
f=0.3

Protocol

1. Make separate solutions of PEG-DA and PEG (100 mg/mL both) in phosphate-buffered saline (PBS). Make a solution of Irgacure 2959 (50 mg/mL) in an ethanol solution (70% v/v) in deionized water.
2. Add 700 μL of the PEG solution to a well in a 12-well plate. Add 300 μL of PEG-DA solution to the PEG solution and mix well. Add 10 μL of Irgacure 2959 solution to the solution of PEG and PEG-DA.
3. Place the 12-well plate under a UV light source from EXFO UV curing system. The sides of the apparatus are covered in aluminum foil to not only protect the observers from the UV light but also to reflect the UV light to the inside. The intensity of the light falling at the bottom of the plate is adjusted to 10 mW/cm$^2$ by manipulating the intensity knob and the height of the light source from the bottom of the plate.
4. The plate is then placed so that the UV beam emanating from the light source is centered at the center of the well containing the above-prepared solution. The UV light is shone for 200 s at which point the gelation is complete.
5. The gel thus prepared is then incubated in PBS (~8 mL) at 37° C. in one of the wells of a 6-well plate for 24 hours. A biological incubator at a temperature of 37° C. and an atmosphere of 5% $CO_2$ is used for the incubation.
6. After the incubation is complete, the gel is put in the bore of a Luer-lok syringe (3 mL or 5 mL). The gel is sheared through the opening of the syringe into another Luer-lok syringe (3 mL or 5 mL), and the process is repeated to get the hydrogel back into the first syringe.
7. The above shearing process is repeated using needles of decreasing bore size progressively. Specifically, 16 gauge, 18 gauge, 20 gauge, and 22 gauge needles are used successively with the hydrogels sheared through each needle twice.
8. The hydrogel thus obtained at the end of the shearing process is added into the bore of an unused, new Luer-lok syringe (3 mL or 5 mL) and capped with an unused, new 16 gauge needle. The gel-containing syringe can be stored at room temperature for a period of 24-48 hours. Storage at 4° C. is recommended for long-term use.
9. If sterile hydrogels are to be prepared, the entire gelling apparatus is moved into a biological hood. Disinfection is carried out by cleaning the equipments with a 70% ethanol solution (v/v). Sterile technique is used for handling the hydrogels and other equipments. The following modifications are made to the above-described protocol when making sterile hydrogels:
   a. The solutions of the as-obtained polymers are made using sterile PBS in autoclaved vials and are not filtered through syringe filters. The photoinitiator solution, on the other hand, is filtered through a syringe filter (0.2 μm) before use.
   b. Hydrogels are formed in sterile 12-well plates and handled using autoclaved forceps.

c. Once the hydrogel is formed using the above mentioned procedure, the hydrogel is further disinfected by incubation in a 70% ethanol solution (v/v) made in sterile deionized water. The hydrogel is incubated for 1 min in 8 mL of 70% ethanol placed in a well of a sterile 6-well plate. The incubation is repeated a total of 3 times using fresh ethanol solution every time.

d. The hydrogel disinfected by incubation in 70% ethanol is then incubated in sterile PBS (8 mL) in a well of a sterile 6-well plate for 5 min. The incubation is repeated a total of 3 times using fresh sterile PBS every time to remove the ethanol absorbed by the gel. Higher incubation times may also be used if the gel seems to have retained more alcohol (the gel look shriveled upon absorption of alcohol).

e. After removing the ethanol, the hydrogel is incubated in fresh, sterile PBS (8 mL) in a new sterile 6-well plate for 24 hours. The PBS in the well is replaced after 12 hours of incubation with fresh sterile PBS (8 mL) by removing the gel (using autoclaved forceps) and putting it in a new sterile 6-well plate containing sterile PBS.

f. The hydrogel is then sheared using the procedure outlined in steps 6 and 7 above. The only difference is that the shearing is carried out using sterile syringes and needles and inside a biological hood.

10. We have prepared several different gels using the procedure outlined above along with independently and systematically changing X, Y, f, $C_X$, $C_Y$, $M_X$, and $M_Y$. e.g.:

a. X=Polyethylene Glycol Diacrylate from SunBio Inc.
Y=Hyaluronic Acid from Genzyme
$M_X$=10 kDa
$M_Y$=560 kDa
$C_X$=100 mg/mL
$C_Y$=1 mg/mL
f=0.27 b. X=Polyethylene Glycol Diacrylate from SunBio Inc.
Y=Dextran
$M_X$=10 kDa
$M_Y$=200 kDa
$C_X$=100 mg/mL
$C_Y$=20 mg/mL
f=0.3

Other hydrogels that have been prepared using the above protocol are listed in the table below.

| Name | Cross-linkable component (X) | Non-crosslinkable component (Y) | Volumetric fraction of X before gelation (f) | Elastic Shear Modulus G' (Pa) |
|---|---|---|---|---|
| PEG-HA | PEG-diacrylate (10 kDa) from SunBio Conc.: 100 mg/mL | Hyaluronic Acid (HA; 74 kDa) from LifeCore Biomedical Conc.: 1 mg/mL | 0.3 | 22 Pa |
| PEG-Dextran | PEG-diacrylate (10 kDa) from SunBio Conc.: 100 mg/mL | Dextran (100 to 200 kDa) from Sigma Conc.: 20 mg/mL | 0.3 | 24 Pa |
| PEG-Alginate | PEG-diacrylate (10 kDa) from SunBio Conc.: 100 mg/mL | Sodium alginate (viscosity: 20,000 to 40,000 cps) from Aldrich Conc.: 0.5 mg/mL | 0.28 | 25 Pa |
| PEG-Polylysine | PEG-diacrylate (10 kDa) from SunBio Conc.: 100 mg/mL | Poly-L-Lysine (70 to 150 kDa) from Fluka Biochemika | 0.28 | 21 Pa |
| HA methacrylate-HA | HA methacrylate synthesized using HA (75 kDa) from LifeCore Biomedical Conc.: 20 mg/mL | Hyaluronic Acid (HA; 64 kDa) from LifeCore Biomedical Conc.: 20 mg/mL | 0.7 | 24 Pa |

Example 2

Figure 3:
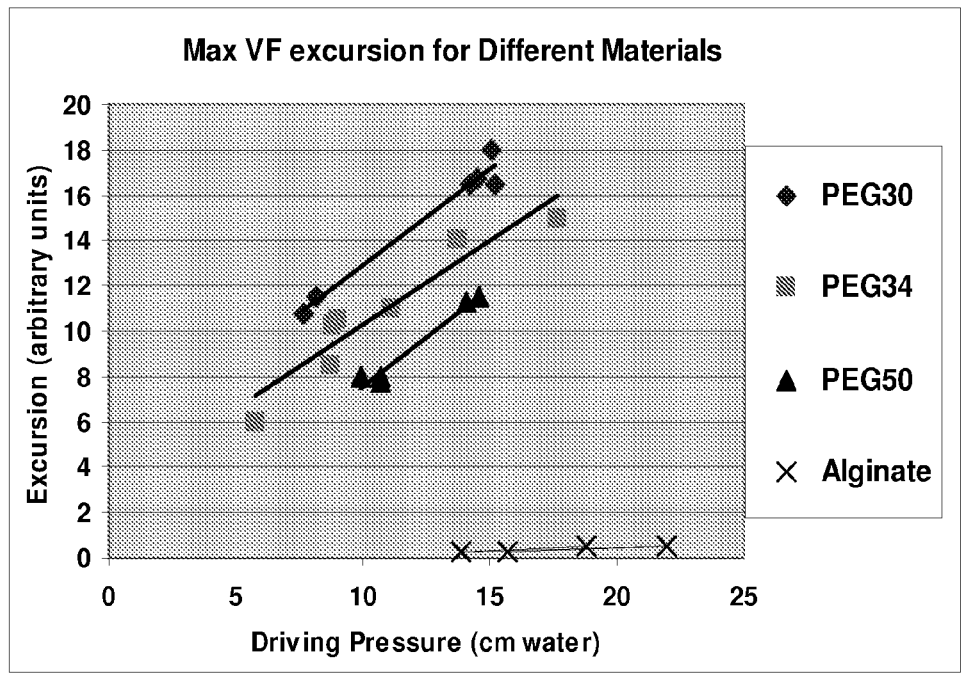
FIG. 3. Differentiation between material stiffness based on their ability to produce vocal fold excursion in a cow larynx model.

Demonstration of the Efficacy of Hydrogels in Repairing the Pliability of the Phonatory Mucosa Using Ex Vivo Models Cow Larynx Model. An ex vivo bovine larynx model was used to the evaluate effects of gel stiffness on mucosal wave amplitude, as a measure of vocal fold pliability. Adult cow cadaver larynges were prepared by cutting a 1 cm by 3 cm window in the thyroid lamina and then removing a block of the thyroarytenoid muscle to expose the deep surface of the vocal ligament, a layer of collagenous tissue between the SLP and the thyroarytenoid muscle. The ligament was opened with microscissors and the soft contents of the lamina propria were carefully removed over the entire extent of the vocal fold, leaving only the thin and transparent epithelium with minimal attached SLP. The test materials were layered behind the epithelium in volumes equal to the volume of the removed lamina propria (~0.25 ml), resulting in a layer of gel 2-3 mm thick. An oval piece of stiff latex sheet was placed behind the test material in the location previously occupied by the vocal ligament. The remaining cavity through the muscle and thyroid cartilage was then filled with stiff alginate for measurement of mucosal wave amplitude using high speed imaging. The alginate, dam, and test material were easily removed for sequential testing of different hydrogels in the same biomechanical environment. PEG30 (G'=25 Pa), PEG34 (G'=121 Pa), and PEG50 (G'=566 Pa) were prepared and tested. As a control, the vocal fold was also filled only with the alginate to create a stiff condition to ensure that an insignificant amount of SLP remained. All materials were tested in the same larynx with each material tested twice. Multiple high speed video clips from tests controlled for subglottal pressure were selected and maximum mid-membranous vocal fold excursion was measured in a blinded manner by two observers. VF excursion was highly correlated with driving pressure for each of the gels (FIG. 3), and this model was sensitive to gel stiffness. As shown in FIG. 3, PEG30 supported more vocal fold excursion than the stiffer gels, with the alginate-filled condition showing very little movement.

Testing of vocal-fold implant materials biomechanically equivalent to PEG30. Different hydrogels biomechanically similar to PEG30 (as judged by measuring their elastic shear modulus, G') were prepared by systematically varying the concentration, volumetric ratio in the precursor solution, and the polymer used for the crosslinkable and non-crosslinkable component. We were able to identify five materials that may be considered mechanically equivalent to PEG30 based on elastic shear modulus (see table in Example 1). These materials were also tested in the cow larynx model using the procedure outlined above. In addition to the hydrogels and alginate we also tested RESTYLANE® (hyaluronic acid), a commercially available dermal filler that has been used for application in the vocal folds. All the materials were tested in a single cow larynx with each material being tested twice. Multiple high speed video clips from tests controlled for sub-glottal pressure were selected and maximum mid-membranous vocal fold excursion was measured using a MATLAB program.

Figure 4:
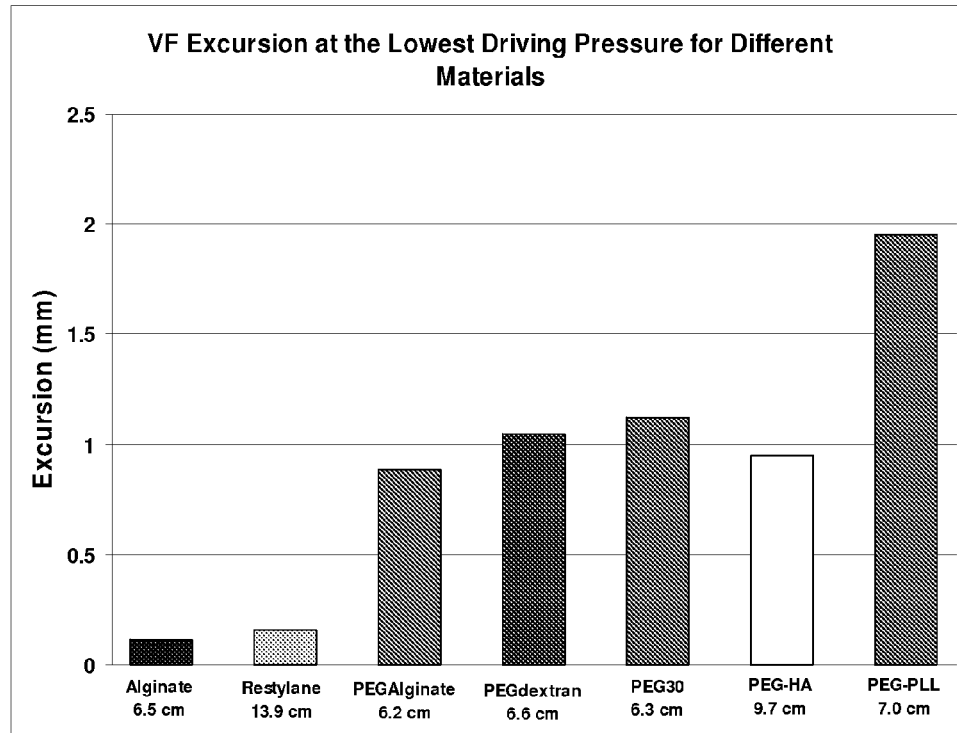
FIG. 4. Vocal fold excursion in a cow larynx model upon implantation of different materials.

FIG. 4 shows the maximum vocal fold (VF) excursion for the different materials at the lowest driving pressure that was able to produce vibration in the VFs. It is important to note that the VF excursion in case of Restylane and PEG-HA were measured at driving pressures of 13.9 cm and 9.7 cm, respectively, while those for the other materials were measured at pressures of approximately 6.5 cm. A high value of the lowest driving pressure required to initiate phonation indicates a comparatively higher stiffness for the material being tested than those with lower values of the lowest driving pressure.

All the materials developed in our labs supported VF excursions greater than that of alginate or Restylane. In addition, the VF excursion supported by the materials was similar in magnitude thereby suggesting that all of these materials are biomechanically suitable for repairing the phonatory mucosa of the vocal folds.

Example 3

Demonstration of Safety and Efficacy of PEG30 in an In Vivo Model

Testing in canines. PEG30 was injected unilaterally in sixteen normal canine VFs with post-injection survival periods of 1, 2, 3, and 4 months (n=4/time point). An average of 60 µL of PEG30 was injected in the VF. We made periodic examinations of VF appearance and in vivo function using methods developed at the MGH Center for Laryngeal Surgery and Voice Rehabilitation. Stroboscopic and high speed videos of the VF vibration (4000 frames/sec) were recorded during these exams while using a tracheal needle to inject air for phonation. These recordings allow us to assess the pliability of the VFs under physiological conditions. High resolution MRI and histology were performed on the excised larynges after euthanasia to identify the location of the PEG30 in the VF and to observe tissue responses to the injected material.

Figure 5:
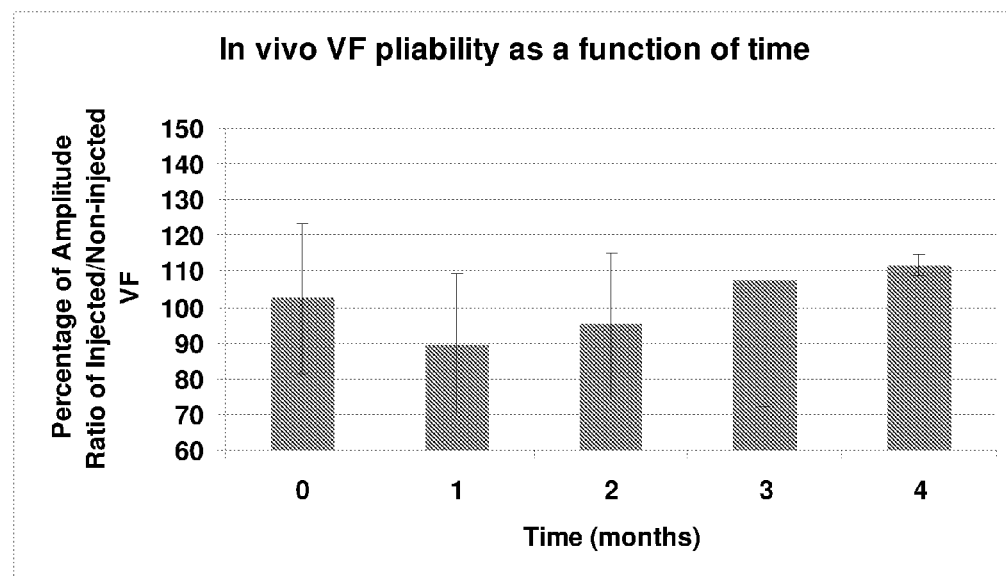
FIG. 5. Percentage of amplitude ratio of the PEG30-injected vocal fold to the non-injected vocal fold as a function of time measured in vivo using a canine model.

Ability of PEG30 to maintain the pliability of vocal folds in vivo. As a measure of VF pliability, the amplitude of VF vibration was measured from the high-speed videos (HSV) collected in the in vivo setting during the periodic exams. The ratio of amplitude of vibration on the injected and non-injected side was compared at each in vivo testing time point. FIG. 5 shows the average percentage of amplitude ratio of the PEG30-injected VF to the non-injected VF over a period of 4 months. Each time point is an average of at least 3 measures obtained from a total of 7 canines. There was no statistical difference between the amplitude ratio measures at all time points tested thereby demonstrating minimal perturbation in pliability of the PEG30-injected VFs as compared to the non-injected VF. In vivo examination of the canine VFs using an operating microscope revealed little or no signs of inflammation in the animals tested. Apart from a few animals where mild redness of the injected VF was observed transiently in the first week or two after the injection, the injected VF surface looked identical to the non-injected VF under high magnification.

Histological analysis of the vocal folds showed that PEG30 generates a foreign-body reaction in the animal VFs characterized by presence of macrophages that actively engulf the PEG30. However, the presence of PEG30 and the associated reaction did not compromise the vibration of the VFs. The PEG30 resorbed and the foreign body reaction resolved almost completely by the end of 16 weeks with no apparent damage to the VF pliability. Overall the injection of PEG30 in the VFs did not cause any adverse tissue reaction nor hinder the normal vibration of the VFs. These results therefore suggest the potential utility of PEG30 as a vocal fold implant to repair the pliability of the phonatory mucosa.

Example 4

Figure 6:
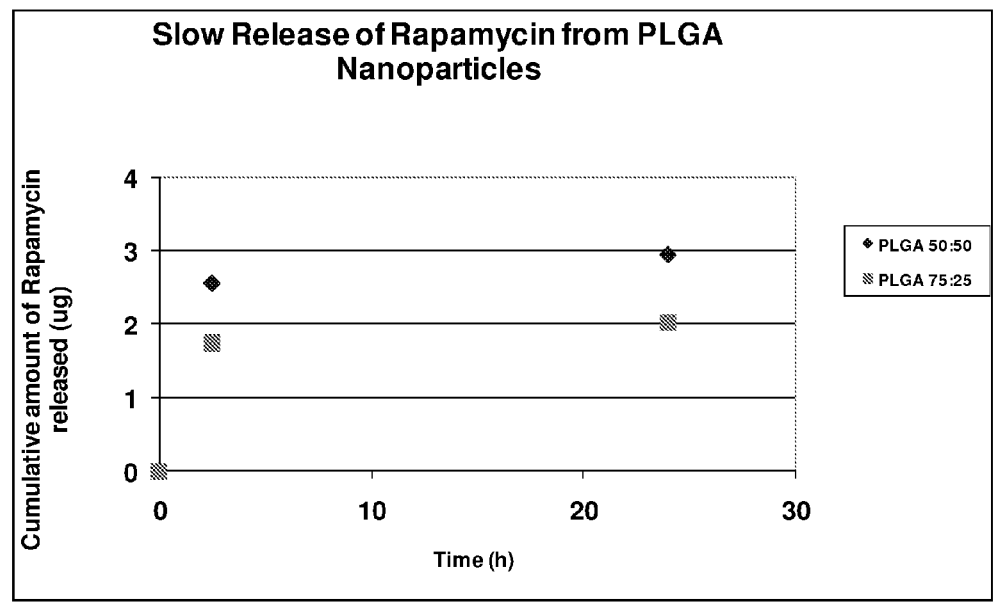
FIG. 6. Slow release of rapamycin from PLGA (50:50; 75:25) nanoparticles in buffer.

Incorporation of Therapeutics in the Hydrogel for Slow Release in the Vocal Folds Poly-L-lactic-co-glycolic acid (PLGA) nanoparticles (NPs) that incorporate rapamycin, an anti-fibrotic drug were made using single emulsion technique. This technique has been used to prepare numerous other drug-loaded PLGA nanoparticles. Rapamycin-loaded NPs were made using two PLGA polymers with different lactic:glycolic acid ratio: PLGA 75:25 and PLGA 50:50 with lactic:glycolic acid ratio of 75:25 and 50:50, respectively. As shown in FIG. 6, the rate of release of rapamycin from PLGA 75:25 NPs in an aqueous buffer is lower than that from PLGA 50:50 NPs for the same amount of total drug loaded. The rate of degradation of PLGA 75:25 in buffer is slower than that of PLGA 50:50. Consequently, rapamycin-loaded NPs made using PLGA 75:25 were expected to release the drug slower than those made using PLGA 50:50. The rapamycin-loaded PLGA 50:50 NPs approximately 200 nm in size were loaded in PEG30 hydrogels by incorporating the NPs in the precursor solution prior to gelation. PLGA 50:50-PEG30 gels containing up to 8 mg/mL (in the precursor solution) of the rapamycin-loaded PLGA NPs had biomechanical properties similar to PEG30 not containing any NPs. This result suggests that PEG30 may be used to not only repair the pliability of the phonatory mucosa but also release therapeutics such as rapamycin in the vocal folds. The process of making drug-loaded PLGA NPs is amenable to incorporation and slow release of a wide variety of drugs. Furthermore, the ease with which these NPs can be incorporated in our hydrogels without compromising their favorable mechanical properties leads us to believe that a variety of drug-eluting, biomechanically relevant hydrogels may be prepared specifically for use in the vocal folds.

Equivalents and Scope

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. For example, it is to be understood that any of the compositions of the invention can be used for vocal cord repair or other soft tissue repair or augmentation. It is also to be understood that any of the compositions made according to the methods for preparing compositions disclosed herein can be used for vocal cord repair or other soft tissue repair or augmentation. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A method of treating a subject having a phonatory mucosa with diminished functional vibratory capacity and diminished phonation, the method comprising
    locating a phonatory mucosa with diminished functional vibratory capacity in the subject; and
    injecting into the phonatory mucosa a hydrogel material that comprises an elastic shear modulus ranging from about 15 to about 121 Pa measured at a frequency of 10 Hz in an amount effective to increase functional vibratory capacity of the phonatory mucosa and improve phonation;
    wherein the hydrogel material comprises a first cross-linked polymer and a second polymer,
        wherein the first cross-linked polymer comprises a cross-linked form of a polyether, polypeptide, or polysaccharide, and
        wherein the second polymer is selected from the group consisting of polyethers, polyacrylates, polyesters, polyanhydrides, polyols, polypeptides, polyvinyl alcohols, proteins, polysaccharides, gelatins, elastins, collagens, celluloses, methylcelluloses, hyaluronic acid, dextrans, alginates, and derivatives thereof,
    and wherein the hydrogel material comprises an interpenetrating or semi-interpenetrating network of the first and second polymers.

2. The method of claim 1, wherein the phonatory mucosa is a part of a vocal cord of the subject.

3. The method of claim 2, wherein the hydrogel material is injected into a superficial lamina propria of the phonatory mucosa.

4. The method of claim 1, wherein the phonatory mucosa is part of the larynx.

5. The method of claim 1, wherein a superficial lamina propria is missing from the phonatory mucosa.

6. The method of claim 1, wherein the first cross-linked polymer comprises a cross-linked form of polyethylene glycol, polylysine, or hyaluronic acid.

7. The method of claim 1, wherein the hydrogel material comprises crosslinked polyethylene glycol diacrylate (PEG-DA) and polyethylene glycol (PEG) in a ratio of about 30:70.

8. The method of claim 1, wherein the hydrogel material has an elastic shear modulus ranging from about 15 to about 35 Pa measured at a frequency of 10 Hz.

9. The method of claim 1, wherein the hydrogel material has an elastic shear modulus ranging from about 20 to about 30 Pa measured at a frequency of 10Hz.

10. The method of claim 1, wherein the hydrogel material has an elastic shear modulus ranging from about 21 to about 25 Pa measured at a frequency of 10 Hz.

11. The method of claim 1, wherein the first cross-linked polymer comprises an acrylated polymer or a methacrylated polymer of polyethylene glycol, polylysine, or hyaluronic acid.

12. The method of claim 1, wherein the first cross-linked polymer comprises polyethylene glycol diacrylate (PEG-DA); and
the second polymer is selected from the group consisting of polyethylene glycol (PEG), polyols, polyacrylates, polypeptides, poly(lysine), gelatins, elastins, collagens, celluloses, methylcelluloses, polysaccharides, and derivatives thereof.

13. The method of claim 12, wherein the second polymer comprises polyethylene glycol (PEG).

14. The method of claim 13, wherein the molecular weight of the PEG-DA is about 10 to about 20 kDa and the molecular weight of the PEG is about 10 to about 20 kDa.

15. The method of claim 12, wherein the second polymer comprises a polysaccharide.

16. The method of claim 15, wherein the polysaccharide is selected from the group consisting of hyaluronic acids, dextrans, and alginates.

17. The method of claim 12, wherein the second polymer comprises a collagen.

18. The method of claim 1, wherein the
first cross-linked polymer comprises hyaluronic acid methacrylate;
the second polymer is selected from the group consisting of polyethylene glycol (PEG), polypeptides, hyaluronic acid (HA), dextrans, alginates, gelatins, elastins, collagens, celluloses, methylcelluloses, and derivatives thereof; and
wherein the hydrogel material comprises an interpenetrating network of the polymers.

* * * * *